United States Patent [19]

Hauel et al.

[11] Patent Number: 5,135,932

[45] Date of Patent: Aug. 4, 1992

[54] 2-HYDROXYPROPYLAMINO-ALKYL-BENZIMIDAZOLY-5-YL DERIVATIVES AND THEIR USE IN THE TREATMENT OF HEART DISEASE

[75] Inventors: Norbert Hauel, Biberach; Annerose Mauz, Baienfurt; Jacques van Meel, Mittelbiberach; Michael Entzeroth, Warthausen; Rainer Zimmermann, Mittelbiberach; Willi Diederen, Biberach, all of Fed. Rep. of Germany

[73] Assignee: Dr. Karl Thomae GmbH, Biberach an der Riss, Fed. Rep. of Germany

[21] Appl. No.: 530,958

[22] Filed: May 30, 1990

[30] Foreign Application Priority Data

Jun. 1, 1989 [DE] Fed. Rep. of Germany ....... 3917801
Oct. 14, 1989 [DE] Fed. Rep. of Germany ....... 3934436

[51] Int. Cl.$^5$ .................... A61K 31/50; C07D 401/10
[52] U.S. Cl. .................... 514/253; 514/247; 544/238; 544/239; 546/158; 549/512; 549/551; 549/554
[58] Field of Search .................... 514/253, 238

[56] References Cited

U.S. PATENT DOCUMENTS

| | | | |
|---|---|---|---|
| 4,361,563 | 11/1982 | Austel et al. | 544/238 |
| 4,608,383 | 8/1986 | Wiedemann et al. | 544/298 |
| 4,616,018 | 10/1986 | Hagel et al. | 544/238 |
| 4,791,109 | 12/1988 | Clemence | 514/253 |
| 4,843,072 | 6/1989 | Yasuda et al. | 544/239 |
| 4,957,920 | 9/1990 | Morsdorf et al. | 514/252 |
| 5,026,705 | 6/1991 | Prucher et al. | 514/253 |
| 5,082,844 | 1/1992 | Yasuda et al. | 514/253 |

FOREIGN PATENT DOCUMENTS

EP-A0412814 2/1991 European Pat. Off. .

OTHER PUBLICATIONS

Slator et al. Jour. Med. Chem. vol. 31 pp. 345-351 (1988).
Teikoku Hormone, Chem Abstr. vol. 112, Entry 198402e (1990).

*Primary Examiner*—Donald G. Daus
*Attorney, Agent, or Firm*—David E. Frankhouser; Alan R. Stempel; Mary-Ellen M. Timbers

[57] ABSTRACT

The invention relates to new 2-hydroxy-n-propylamines of the formula $$R_1-O-CH_2-CHOH-CH_2-NH-A-R_2 \quad (I)$$

wherein $R_1$, $R_2$ and A are defined as in claim 1, the tautomers, enantiomers and acid addition salts thereof, particularly for pharmaceutical use the physiologically acceptable acid addition salts thereof with inorganic or organic acids, which have valuable pharmacological properties, more particularly a simultaneous cardiotonic and $\beta$-blocking activity, and the use thereof as pharmaceutical compositions and processes for preparing them.

9 Claims, No Drawings

2-HYDROXYPROPYLAMINO-ALKYL-BENZIMIDAZOLY-5-YL DERIVATIVES AND THEIR USE IN THE TREATMENT OF HEART DISEASE

The present invention relates to 2-hydroxy-n-propylamines of the formula

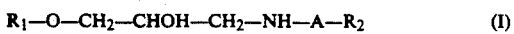

the tautomers, the enantiomers and acid addition salts thereof, more particularly for pharmaceutical use the physiologically acceptable acid addition salts thereof with inorganic or organic acids, the use thereof and processes for preparing them.

The above compounds have valuable pharmacological properties, particularly a simultaneous cardiotonic and $\beta$-blocking activity.

In the above formula I $R_1$ represents a naphthyl group, a 3,4-dihydro-2-hydroxyquinolinyl group bound via the phenyl ring, a phenyl group substituted by a $C_{1-5}$ alkylsulphonyloxy or by an allyl, allyloxy, cyano or aminocarbonylmethyl group, a phenyl group substituted by a $C_{1-3}$ alkyl group, wherein the alkyl moiety is substituted in the 1-, 2- or 3-position by an alkoxy, cycloalkyloxy, cycloalkylmethoxy, 2-alkoxyethoxy, 2-cycloalkyloxyethoxy, 2-cycloalkylmethoxy-ethoxy or 2-phenoxyethoxy group, wherein the alkoxy moiety may contain from 1 to 6 carbon atoms and the cycloalkyl or cycloalkyloxy part may contain 3 to 6 carbon atoms, or a phenyl group disubstituted by a $C_{1-3}$ alkyl group and by a halogen atom, A represents a straight-chained $C_{2-4}$ alkylene group optionally substituted by one or two $C_{1-3}$ alkyl groups and $R_2$ represents a group of formula

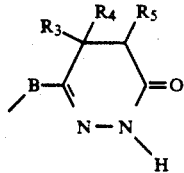

wherein $R_3$ represents a hydrogen atom or a $C_{1-3}$ alkyl group,
$R_4$ and $R_5$ each represent a hydrogen atom or together represent another carbon-carbon bond and
B represents a group of the formula

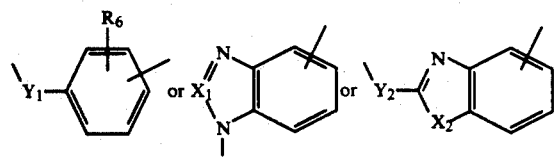

wherein $R_6$ represents a $C_{1-3}$ alkyl group or a hydrogen or halogen atom,
$Y_1$ represents a bond, an oxygen atom, a sulphonyl group or an —NH—CO—CH$_2$ group wherein the CH$_2$ moiety is attached to the phenyl nucleus, $X_1$ represents a nitrogen atom or a methyne group optionally substituted by a hydroxy group or by a $C_{1-3}$ alkyl group,
$X_2$ represents an oxygen atom or an imino group and
$Y_2$ represents a bond or an imino group.

As examples of the definitions for the groups given hereinbefore:

R may represent a 1-naphthyl, 2-napthyl, 3,4-dihydro-2-hydroxy-quinolin-5-yl, 3,4-dihydro-2-hydroxy-quinolin-6-yl, 3,4-dihydro-2-hydroxy-quinolin-7-yl, 3,4-dihydro-2-hydroxy-quinolin-8-yl, 4-methylsulphonyloxy-phenyl, 4-ethylsulphonyloxy-phenyl, 4-n-propylsulphonyloxy-phenyl, 4-isopropylsulphonyloxy-phenyl, 4-n-butylsulphonyloxyphenyl, 4-n-pentylsulphonyloxy-phenyl, 4-isobutylsulphonyloxy-phenyl, 4-tert.pentylsulphonyloxyphenyl, 2-allyl-phenyl, 4-allyl-phenyl, 2-allyloxy-phenyl, 4-allyloxy-phenyl, 2-cyanophenyl, 3-cyanophenyl, 4-cyano-phenyl, 2-aminocarbonylmethyl-phenyl, 3-aminocarbonylmethyl-phenyl, 4-aminocarbonylmethylphenyl, 4-(methoxymethyl)phenyl, 4-(ethoxymethyl)phenyl, 4-(n-propoxymethyl)phenyl, 4-(isopropoxymethyl)phenyl, 4-(cyclopropyloxymethyl)-phenyl, 4-(n-butyloxymethyl)phenyl, 4-((2-methyl-n-propoxy)methyl)phenyl, 4-(n-pentyloxymethyl)-phenyl, 4-(n-hexyloxymethyl)phenyl, 4-(cyclopropylmethoxy-methyl)phenyl, 4-(cyclobutyloxymethyl)phenyl, 4-(cyclobutyloxymethyl-methyl)phenyl, 4-(cyclopentyloxy-methyl)phenyl, 4-(cyclopentylmethoxymethyl)phenyl, 4-(cyclohexyloxymethyl)phenyl, 4-(cyclohexylmethoxymethyl)-phenyl, 4-(2-methoxyethyl)phenyl, 4-(2-ethoxyethyl)-phenyl, 4-(2-n-propoxyethyl)phenyl, 4-(2-isopropoxy-ethyl)phenyl, 4-(2-n-butoxy-ethyl)phenyl, 4-(2-(2-methyl-n-propoxy)ethyl)phenyl, 4-(2-n-pentyloxyethyl)-phenyl, 4-(2-n-hexyloxyethyl)phenyl, 4-(2-cyclopropyloxy-ethyl)-phenyl, 4-(2-cyclopropylmethoxy-ethyl)phenyl, 4-(2-cyclobutyloxyethyl)phenyl, 4-(2-cyclobutylmethoxy-ethyl)phenyl, 4-(2-cyclopentyloxy-ethyl)phenyl, 4-(2-cyclopentylmethoxyethyl)phenyl, 4-(2-cyclohexyloxy-ethyl)phenyl, 4-(2-cyclohexylmethoxy-ethyl)-phenyl, 4-(3-methoxypropyl)phenyl, 4-(3-ethoxypropyl)phenyl, 4-(3-n-propoxypropyl)phenyl, 4-(3-isopropoxypropyl)phenyl, 4-(3-n-butoxypropyl)phenyl, 4-(3-(2-methyl-n-propoxy)propyl)phenyl, 4-(3-n-pentyloxypropyl)phenyl, 4-(3-n-hexyloxypropyl)phenyl, 4-(3-cyclopropyloxypropyl)phenyl, 4-(3-cyclopropylmethoxy-propyl), 4-(3-cyclobutyloxy-propyl)-phenyl, 4-(3-cyclobutylmethoxypropyl)phenyl, 4-(3-cyclopentyloxy-propyl)phenyl, 4-(3-cyclopentylmethoxy-propyl)phenyl, 4-(3-cyclohexyloxypropyl)phenyl, 4-(3-cyclohexylmethoxy-propyl)phenyl, 4-((2-methoxyethoxy)methyl)phenyl, 4-((2-ethoxyethoxy)-methyl)phenyl, 4-((2-n-propoxyethoxy)methyl)phenyl, 4-((2-isopropoxyethoxy)methyl)phenyl, 4-((2-n-butoxyethoxy)methyl)phenyl, 4-((2-(2-methyl-n-propoxy)ethoxy)methyl)phenyl, 4-((2-n-pentyloxyethoxy)methyl)phenyl, 4-((2-n-hexyloxyethoxy)methyl)phenyl, 4-((2-cyclopropyloxyethoxy)methyl)-phenyl, 4-((2-cyclopropylmethoxy-ethoxy)methyl)-phenyl, 4-((2-cyclobutyloxyethoxy)-methyl)phenyl, 4-((2-cyclobutylmethoxy-ethoxy)methyl)-phenyl, 4-((2-cyclopentyloxyethoxy)methyl)phenyl, 4-((2-cyclopentylmethoxyethoxy)methyl)phenyl, 4-((2-cyclohexyloxyethoxy)methyl)phenyl, 4-((2-cyclohexylmethoxy-ethoxy)methyl)phenyl, 4-(2-(2-methoxyethoxy)-ethyl)phenyl, 4-(2-(2-ethoxyethoxy)ethyl)phenyl, 4-(2-(2-n-propoxyethoxy)ethyl)phenyl, 4-(2-(2-isopropoxyethoxy)ethyl)phenyl, 4-(2-(2-n-butoxyethoxy)ethyl)phenyl, 4-(2-(2-(2-methyl-n-propoxy)ethoxy)ethyl)phenyl, 4-(2-(2-n-pentyloxyethoxy)ethyl)phenyl, 4-(2-(2-n-hexyloxyethoxy)ethyl)-phenyl, 4-(2-(2-cyclopropyloxyethoxy)-ethyl)phenyl, 4-(2-(2-cyclopropylmethoxyethoxy)ethyl)-phenyl, 4-(2-(2-cyclobutyloxyethoxy)ethyl)phenyl, 4-(2-(2-cyclobutylmethoxyethoxy)ethyl)phenyl, 4-(2-(2-cyclopentyloxyethoxy)ethyl)phenyl, 4-(2-(2-cyclopentylmethoxyethoxy)ethyl)phenyl, 4-(2-(2-cyclohexyloxyethoxy)ethyl)phenyl, 4-(2-(2-cyclohexylmethoxyethoxy)ethyl)phenyl, 4-(3-(2-methoxyethoxy)propyl)phenyl, 4-(3-(2-ethoxyethoxy)propyl)phenyl, 4-(3-(2-n-propoxyethoxy)propyl)-phenyl, 4-(3-(2-isopropoxyethoxy)propyl)phenyl, 4-(3-(2-n-butoxyethoxy)propyl)phenyl, 4-(3-(2-(2-methyl-n-propoxy)ethoxy)propyl)phenyl, 4-(3-(2-n-pentyloxyethoxy)propyl)phenyl, 4-(3-(2-n-hexyloxyethoxy)-propyl)phenyl, 4-(3-(2-cyclopropyloxyethoxy)propyl)phenyl, 4-(3-(2-cyclopropylmethoxyethoxy)propyl)phenyl, 4-(3-(2-cyclobutyloxyethoxy)-propyl)phenyl, 4-(3-(2-cyclobutylmethoxyethoxy)-propyl)phenyl, 4-(3-(2-cyclopentyloxy-ethoxy)-propyl)phenyl, 4-(3-(2-cyclopentylmethoxyethoxy)-propyl)phenyl, 4-(3-(2-cyclohexyloxyethoxy)-propyl)phenyl, 4-(3-(2-cyclohexylmethoxyethoxy)-propyl)phenyl, 4-((2-phenoxyethoxy)methyl)phenyl, 4-(2-(2-phenoxyethoxy)ethyl)phenyl, 4-(3-(2-phenoxyethoxy)propyl)phenyl, 2-chloro-3-methyl-phenyl, 2-chloro-4-methyl-phenyl, 2-chloro-5-methyl-phenyl, 2-chloro-6-methyl-phenyl, 3-chloro-2-methyl-phenyl, 3-chloro-4-methyl-phenyl, 3-chloro-5-methyl-phenyl, 3-chloro-6-methyl-phenyl, 4-chloro-2-methyl-phenyl, 4-chloro-3-methyl-phenyl, 2-fluoro-3-methyl-phenyl, 2-fluoro-4-methyl-phenyl, 2-fluoro-5-methyl-phenyl, 2-fluoro-6-methyl-phenyl, 3-fluoro-2-methyl-phenyl, 3-fluoro-4-methyl-phenyl, 3-fluoro-5-methyl-phenyl, 3-fluoro-6-methyl-phenyl, 4-fluoro-2-methyl-phenyl, 4-fluoro-3-methyl-phenyl, 2-bromo-3-methyl-phenyl, 2-bromo-4-methyl-phenyl, 2-bromo-5-methyl-phenyl, 2-bromo-6-methyl-phenyl, 3-bromo-2-methyl-phenyl, 3-bromo-4-methyl-phenyl, 3-bromo-5-methyl-phenyl, 3-bromo-6-methyl-phenyl, 4-bromo-2-methyl-phenyl or 4-bromo-3-methyl-phenyl group, A may represent an ethylene, n-propylene, n-butylene, α-methyl-ethylene, α-methyl-n-propylene, α-methyl-n-butylene, α,α-dimethyl-ethylene, α,α-dimethyl-n-propylene, α,α-dimethyl-n-butylene, α,α-diethylethylene, α,α-diethyl-n-propylene, α,α-diethyl-n-butylene, α-methyl-α-ethyl-ethylene, α-methyl-α-ethyl-n-propylene, α-methyl-α-ethyl-n-butylene, α-methyl-α-n-propyl-ethylene, α-methyl-α-n-propyl-n-propylene or α-ethyl-α-n-propyl-n-propylene group and $R_2$ may represent a 3-(3(2H)-pyridazinon-6-yl)phenoxy, 4-(3-(2H)-pyridazinon-6-yl)phenoxy, 3-(4,5-dihydro-3(2H)-pyridazinon-6-yl)phenoxy, 3-(4,5-dihydro-5-methyl-3(2H)-pyridazinon-6-yl)phenoxy, 3-(4,5-dihydro-5-ethyl-3(2H)-pyridazinon-6-yl)phenyl, 3-(4,5-dihydro-5-isopropyl-(3(2H)-pyridazinon-6-yl)phenoxy, 4-(4,5-dihydro-3(2H)-pyridazinon-6-yl)phenoxy, 4-(4,5-dihydro-5-methyl-3(2H)-pyridazinon-6-yl)phenoxy, 4-(4,5-dihydro-5-ethyl-3(2H)-pyridazinon-6-yl)phenoxy, 4-(4,5-dihydro-5-isopropyl-3(2H)-pyridazinon-6-yl)phenoxy, 2-methyl-3-(3(2H)-pyridazinon-6-yl)phenoxy, 2-methyl-4-(3(2H)-pyridazinon-6-yl)phenoxy, 2-methyl-3-(4,5-dihydro-3(2H)-pyridazinon-6-yl)phenoxy, 2-methyl-3-(4,5-dihydro-5-methyl-3(2H)-pyridazinon-6-yl)phenoxy, 2-methyl-3-(4,5-dihydro-5-ethyl-3(2H)-pyridazinon-6-yl)phenoxy, 2-methyl-3-(4,5-dihydro-5-isopropyl-3(2H)-pyridazinon-6-yl)phenoxy, 2-methyl-4-(4,5-dihydro-3(2H)-pyridazinon-6-yl)phenoxy, 2-methyl-4-(4,5-dihydro-5-methyl-3(2H)-pyridazinon-6-yl)phenoxy, 2-methyl-4-(4,5-dihydro-5-ethyl-3(2H)-pyridazinon-6-yl)phenoxy, 2-methyl-4-(4,5-dihydro-5-isopropyl-3(2H)-pyridazinon-6-yl)phenoxy, 2-chloro-4-(3(2H)-pyridazinon-6-yl)phenoxy, 2-chloro-4-(4,5-dihydro-3(2H)-pyridazinon-6-yl)phenoxy, 2-chloro-4-(4,5-dihydro-5-methyl-3(2H)-pyridazinon-6-yl)phenoxy, 2-chloro-4-(4,5-dihydro-5-ethyl-3(2H)-pyridazinon-6-yl)phenoxy, 2-chloro-4-(4,5-dihydro-5-isopropyl-3(2H)-pyridazinon-6-yl)phenoxy, 5-(3(2H)-pyridazinon-6-yl)-benzoxazol-(2)-imino, 5-(4,5-dihydro-3(2H)-pyridazinon-6-yl)benzoxazol-(2)-imino, 5-(4,5-dihydro-5-methyl-3(2H)-pyridazinon-6-yl)benzoxazol-(2)-imino, 5-(4,5-dihydro-5-ethyl-3(2H)-pyridazinon-6-yl)benzoxazol-(2)-imino, 5-(4,5-dihydro-5-isopropyl-3(2H)-pyridazinon-6-yl)benzoxazol-(2)-imino, 5-(3(2H)-pyridazinon-6-yl)benzimidazol-1-yl, 5-(4,5-dihydro-3(2H)-pyridazinon-6-yl)benzimidazol-1-yl, 5-(4,5-dihydro-5-methyl-3(2H)-pyridazinon-6-yl)benzimidazol-1-yl, 5-(4,5-dihydro-5-ethyl-3(2H)-pyridazinon-6-yl)benzimidazol-1-yl, 5-(4,5-dihydro-5-isopropyl-3(2H)-pyridazinon-6-yl)-benzimidazol-1-yl, 5-(3(2H)-pyridazinon-6-yl)-benzimidazol-2-yl, 5-(4,5-dihydro-3(2H)-pyridazinon-6-yl)-benzimidazol-2-yl, 5-(4,5-dihydro-5-methyl-3(2H)-pyridazinon-6-yl)benzimidazol-2-yl, 5-(4,5-dihydro-5-ethyl-3(2H)-pyridazinon-6-yl)benzimidazol-2-yl, 5-(4,5-dihydro-5-isopropyl-3(2H)-pyridazinon-6-yl)benzimidazol-2-yl, 5-(3(2H)-pyridazinon-6-yl)-2-methyl-benzimidazol-1-yl, 5-(4,5-dihydro-3(2H)-pyridazinon-6-yl)-2-methylbenzimidazol-1-yl, 5-(4,5-dihydro-5-methyl-3(2H)-pyridazinon-6-yl)-2-methyl-benzimidazol-1-yl, 5-(4,5-dihydro-5-ethyl-3(2H)-pyridazinon-6-yl)-2-methylbenzimidazol-1-yl, 5-(4,5-dihydro-5-isopropyl-3(2H)-pyridazinon-6-yl)-2-methyl-benzimidazol-1-yl, 5-(4,5-dihydro-3(2H)-pyridazinon-6-yl)-2-hydroxy-benzimidazol-1-yl, 5-(4,5-dihydro-5-methyl-3(2H)-pyridazinon-6-yl)-2-hydroxy-benzimidazol-1-yl, 5-(4,5-dihydro-5-ethyl-3(2H)-pyridazinon-6-yl)-2-hydroxy-benzimidazol-1-yl, 5-(4,5-dihydro-5-isopropyl-3(2H)-pyridazinon-6-yl)-2-hydroxy-benzimidazol-1-yl, 5-(3(2H)-pyridazinon-6-yl)benztriazol-1-yl, 5-(4,5-dihydro-3(2H)-pyridazinon-6-yl)benztriazol-1-yl, 5-(4,5-dihydro-5-methyl-3(2H)-pyridazinon-6-yl)benztriazol-1-yl, 5-(4,5-dihydro-5-ethyl-3(2H)-pyridazinon-6-yl)benztriazol-1-yl, 5-(4,5-dihydro-5-isopropyl-3(2H)-pyridazinon-6-yl)benztriazol-1-yl, 4-(3(2H)-pyridazinon-6-yl)phenylsulphonyl, 4-(4,5-dihydro-3(2H)-pyridazinon-6-yl)phenylsulphonyl, 4-(4,5-dihydro-5-methyl-3(2H)-pyridazinon-6-yl)phenylsulphonyl, 4-(4,5-dihydro-5-ethyl-3(2H)-pyridazinon-6-yl)phenylsulphonyl, 4-(4,5-dihydro-5-isopropyl-3(2H)-pyridazinon-6-yl)phenylsulphonyl, 4-(3(2H)-pyridazinon-6-yl)phenyl, 4-(4,5-dihydro-3(2H)-pyridazinon-6-yl)phenyl, 4-(4,5-dihydro-5-methyl-3(2H)-pyridazinon-6-yl)phenyl, 4-(4,5-dihydro-5-ethyl-3(2H)-pyridazinon-6-yl)phenyl, 4-(4,5-dihydro-5-isopropyl-3(2H)-pyridazinon-6-yl)phenyl, 4-(3-(2H)-pyridazinon-6-yl)phenylmethylcarbonylamino, 4-(4,5-dihydro-3(2H)-pyridazinon-6-yl)phenylmethylcarbonylamino, 4-(4,5-dihydro-5-methyl-3(2H)-pyridazinon-6-yl)phenylmethylcarbonylamino, 4-(4,5-dihydro-5-ethyl-3(2H)-pyridazinon-6-yl)phenylmethylcarbonylamino or 4-(4,5-dihydro-5-isopropyl-3(2H)-pyridazinon-6-yl)phenylmethylcarbonylamino group.

Preferred compounds of the above formula are those wherein $R_1$ represents a naphthyl, 3,4-dihydro-2-hydroxy-quinolin-5-yl, allylphenyl, allyloxyphenyl, cyanophenyl, aminocarbonylmethyl-phenyl or chloro-methylphenyl group, an alkylsulphonyloxyphenyl group with 1 to 4 carbon atoms in the alkyl moiety or a phenyl group substituted in the 4-position by a 2-alkoxyethyl, 2-cycloalkylmethoxy-ethyl, 2-alkoxy-ethoxymethyl, 2-cycloalkyloxy-ethoxymethyl, 2-cycloalkylmethoxy-ethoxymethyl or 2-phenoxy-ethoxymethyl group, wherein the alkoxy moiety may contain 1 to 4 carbon atoms and the cycloalkyl or cycloalkyloxy part may contain 3 or 4 carbon atoms, A represents a $C_{2-4}$ n-alkylene group optionally mono- or disubstituted by a methyl group in the α-position with respect to the adjacent nitrogen atom and $R_2$ represents a group of the formula

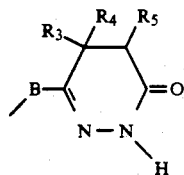

wherein $R_3$ represents a hydrogen atom or a methyl group,
$R_4$ and $R_5$ each represent a hydrogen atom or together represent another carbon-carbon bond and
B represents a group of the formula

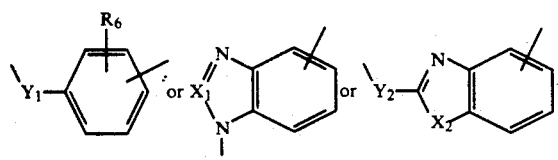

wherein $R_6$ represents a hydrogen, fluorine, chlorine or bromine atom or a methyl group,
Y represents a bond, an oxygen atom or an —NH—CO—CH$_2$— group, the —CH$_2$— moiety being attached to the phenyl nucleus,
$X_1$ represents a nitrogen atom or a methyne group optionally substituted by a hydroxy or methyl group,
$X_2$ represents an oxygen atom or an imino group and
$Y_2$ represents a bond or an imino group,
the tautomers, enantiomers and acid addition salts thereof.

Particularly preferred compounds of formula I above are however those wherein $R_1$ represents a naphthyl, 3,4-dihydro-2-hydroxy-quinolin-5-yl, allylphenyl, allyloxyphenyl or chloromethylphenyl group or a phenyl group substituted in the 4-position by a 2-alkoxyethyl, 2-cycloalkylmethoxyethyl, 2-alkoxyethoxymethyl, 2-cycloalkyloxyethoxymethyl, 2-cycloalkylmethoxyethoxymethyl or 2-phenoxyethoxymethyl group, wherein the alkoxy moiety may contain 1 to 3 carbon atoms and the cycloalkyl or cycloalkyloxy moiety may contain 3 or 4 carbon atoms, A represents a $C_{2-4}$ n-alkylene group optionally disubstituted by methyl groups in the α-position with respect to the adjacent nitrogen atom and $R_2$ represents a group of the formula

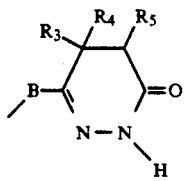

wherein $R_3$ represents a hydrogen atom or a methyl group,
$R_4$ and $R_5$ each represent a hydrogen atom or together represent another carbon-carbon bond and
B represents a group of formula

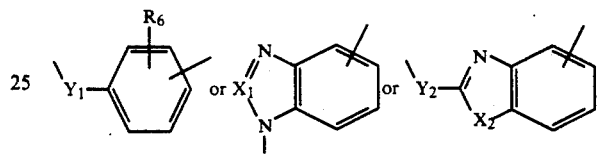

wherein $R_6$ represents a methyl group or a hydrogen or chlorine atom,
$Y_1$ represents an oxygen atom,
$X_1$ represents a methyne group,
$X_2$ represents an oxygen atom or an imino group and
$Y_2$ represents a bond or an imino group,
the tautomers, enantiomers and acid addition salts thereof.

According to the invention the compounds of formula I are obtained by reacting a compound of formula $$R_1\text{—O—CH}_2\text{—CHOH—CH}_2\text{—Z} \quad \text{(II)}$$

(wherein $R_1$ is as hereinbefore defined and Z represents a nucleophilic leaving group such as a halogen atom or a sulphonic acid ester group, e.g. a chlorine, bromine or iodine atom or a methylsulphonyloxy or p-toluenesulphonyloxy group, or Z together with the hydrogen atom of the adjacent hydroxy group represents an oxygen-carbon bond) with an amine of formula $$\text{NH}_2\text{—A—R}_2 \quad \text{(III)}$$

wherein

A and $R_2$ are as hereinbefore defined.

The reaction is preferably carried out in a solvent such as ethanol, isopropanol, tetrahydrofuran, dioxan, benzene, toluene, dimethylformamide or dimethylsulphoxide, optionally in the presence of an acid binding agent such as triethylamine or pyridine, which may simultaneously be used as solvent, at temperatures between 0° and 100° C., but preferably at temperatures between 25° and 80° C.

As the compounds of formula I have at least one chiral centre, they may be resolved by conventional methods into their diastereoisomers, for example by column chromatography, and into their enantiomers, for example by column chromatography on a chiral phase or by crystallisation with optically active acids, e.g. with D- or L-monomethyl tartaric acid, D- or L-diacetyl tartaric acid, D- or L-tartaric acid, D- or L-lactic acid or D- or L-camphoric acid.

Furthermore, the compounds of formula I obtained may if desired be converted into the acid addition salts thereof, more particularly for pharmaceutical use into the physiologically acceptable salts thereof with inorganic or organic acids. Examples of such acids include hydrochloric, hydrobromic, sulphuric, phosphoric, fumaric, succinic, lactic, citric, tartaric or maleic acid.

The compounds of formulae II and III used as starting materials are obtained using methods known from the literature.

Thus, for example, a compound of formula II is obtained by reacting a corresponding phenol with a corresponding epihalohydrin or with a 2-hydroxypropane substituted appropriately in the 1- and 3-positions.

A compound of formula III is obtained by cleavage of an amine of formula III protected by a suitable protecting group, the starting compound required being obtained either by reacting a corresponding 4-oxobutyric acid with hydrazine, by reacting a corresponding 2-methylthio-benzoxazole (see EP-A-34743) with a corresponding amine or by alkylation of a corresponding phenol, thiophenol, benzimidazole or benzotriazole, the thio compound thus obtained subsequently being converted into the corresponding sulphone by oxidation.

As already mentioned hereinbefore, the new 2-hydroxy-n-propylamines of formula I, the tautomers, enantiomers and physiologically acceptable acid addition salts thereof have valuable pharmacological properties, particularly a simultaneous cardiotonic and β-blocking activity.

The following compounds, for example:

A=6-[1-[2-[3-(4-(2-cyclobutylmethoxy-ethyl)phenoxy)-2-hydroxy-propylamino]ethyl]benzimidazol-5-yl]-4,5-dihydro-3(2H)-pyridazinone, B=6-[1-[2-[3-(4-(2-cyclopropylmethoxy-ethyl)phenoxy)-2-hydroxy-propylamino]ethyl]benzimidazol-5-yl]-4,5-dihydro-3(2H)-pyridazinone, C=6-[4-[2-[3-(4-(2-cyclopropylmethoxy-ethyl)phenoxy)-2-hydroxy-propylamino]ethoxy]phenyl]-4,5-dihydro-3(2H)-pyridazinone, D=6-[4-[2-[3-(4-(2-cyclopropylmethoxyethyl)phenoxy)-2-hydroxy-propylamino]ethoxy]phenyl]-3(2H)-pyridazinone, E=6-[4-[2-[3-(4-(2-cyclobutylmethoxy-ethyl)phenoxy)-2-hydroxy-propylamino]ethoxy]phenyl]-4,5-dihydro-3(2H)-pyridazinone, F=6-[4-[2-[3-(4-((2-isopropoxyethoxy)methyl)phenoxy)-2-hydroxy-propylamino]ethoxy]phenyl]-4,5-dihydro-3(2H)-pyridazinone, G=6-[4-[2-[3-(4-(2-isopropoxyethoxymethyl)phenoxy)-2-hydroxypropylamino]ethoxy]phenyl]-3(2H)-pyridazinone, H=6-[1-[3-[3-(4-(2-isobutoxyethyl)phenoxy)-2-hydroxypropylamino]benzimidazol-5-yl]-4,5-dihydro-3(2H)-pyridazinone, I=6-[1-[2-[3-(4-(2-isobutoxyethyl)phenoxy)-2-hydroxypropylamino]-2,2-dimethyl-ethyl]benzimidazol-5-yl]-4,5-dihydro-3(2H)-pyridazinone, K=6-[4-[3-[3-(4-(2-isopropoxyethoxy-methyl)phenoxy)-2-hydroxy-propylamino]propoxy]-3-chloro-phenyl]-4,5-dihydro-3(2H)-pyridazinone, L=6-[4-[2-[3-(4-(2-isopropoxyethoxy-methyl)phenoxy)-2-hydroxy-propylamino]ethoxy]-3-chloro-phenyl]-4,5-dihydro-3(2H)-pyridazinone, M=6-[4-[2-[3-(4-(2-cyclopropylmethoxy-ethyl)phenoxy)-2-hydroxy-propylamino]ethoxy]-3-methyl-phenyl]-4,5-dihydro-3(2H)-pyridazinone, N=6-[4-[2-[3-(4-(2-isopropoxyethoxy-methyl)phenoxy)-2-hydroxy-propylamino]ethoxy]-3-methyl-phenyl]-4,5-dihydro-3(2H)-pyridazinone, O=6-[4-[3-[3-(4-(2-cyclopropylmethoxy-ethyl)phenoxy)-2-hydroxy-propylamino]propoxy]-3-methyl-phenyl]-4,5-dihydro-3(2H)-pyridazinone, P=6-[4-[3-[3-(4-(2-cyclobutylmethoxy-ethyl)phenoxy)-2-hydroxy-propylamino]propoxy]-3-methyl-phenyl]-4,5-dihydro-3(2H)-pyridazinone and Q=6-[4-[2-[3-(4-(2-isopropoxyethoxy-methyl)phenoxy)-2-hydroxy-propylamino]ethoxy]-3-methyl-phenyl]-3(2H)-pyridazinone were investigated for their biological properties as follows:

1. Affinity for β-adreno recectors

The inhibitory effect on the binding of $^3$H-CGP 12177 was tested on receptor preparations from rat hearts ($\beta_1$) and rat lungs ($\beta_2$). The binding assay was carried out with some modifications according to the method of Dämmgen et al. (Drug. Res. 35: 383–390 (1985)). The incubation mixture contained aliquots of the membrane preparation in Tris buffer, increasing concentrations of the potential antagonist as well as 200 pM $^3$H-CGP 12177. The bound and free radioligands were separated after the incubation period by rapid filtration through glass fibre filters. The filter-bound radioactivity was determined in a β counter with a counting yield of about 52%. The non-specific binding was determined in the presence of $10^{-5}$ M propranolol.

| Substance | IC$_{50}$ (nM) $\beta_1$ | $\beta_2$ |
|---|---|---|
| A | 26 | 940 |
| B | 34 | 2300 |
| C | 29 | 1200 |
| D | 22 | 1000 |
| E | 15 | 1100 |
| F | 24 | 7200 |
| G | 53 | 4400 |
| H | 10 | 19 |
| I | 12 | 65 |
| K | 10 | 350 |
| L | 7.6 | 600 |
| M | 0.5 | 100 |
| N | 2.6 | 520 |
| O | 59 | 66 |
| P | 6.0 | 220 |
| Q | 2.0 | 210 |

Cardiotonic effect with antiadrenergic activity

Guinea-pigs (Dunkin-Hartley-Pirbright, male, 450–600 g) were anaesthetised with hexobarbital-sodium (150 mg/kg i.p.). After the animals had become unconscious, a tracheal cannula was inserted and the animals were pitched (van Meel, J. Pharmacol. Methods 31 (1): 1–11 (1985)). The animals were then immediately artificially respirated using a breathing pump. The left ventricular pressure (LVP) was measured with a Millar PR-249 catheter-tip manometer inserted into the left ventricle through the left carotid artery. This pressure signal was differentiated electronically (LV-dP/dtmax) and used as a parameter for inotropia. The arterial blood pressure was recorded by a cannula in the right carotid artery using a Bell & Howell pressure recorder. The heart rate was also measured. The substances were administered through a cannula in the jugular vein.

The test substances were administered to three animals cumulatively in four doses (0.1 to 3 mg/kg) and the effects on blood pressure, heart rate and LV-dP/dtmax were measured. Three minutes after the last dose of the test substance, isoprenalin was administered intravenously in increasing doses. In this way, a cumulative dose-activity correlation was obtained for isoprenalin in the presence of the test substance. The parameters measured were the increase in heart rate and the LV-dP/dtmax. These dose-activity curves were compared with standard curves for isoprenalin without the test substances. The shift to the right of the dose-activity curves for isoprenalin brought about by the test substances were determined graphically and corresponding pA2 values for the test substances were calculated. (see Tenakin in "Pharmacologic Analysis of Drug Receptor Interaction", Rawen Press 1987, pages 211–212).

The Table shows the effects of the test substances after a dose of 3 mg/kg i.v. on the LV-dP/dtmax and heart rate and the calculated pA2 values for the test substances as against the inotropic (pA2 inotropia) and heart rate-increasing (pA2 heart rate) activity of isoprenalin.

The Table which follows contains the averages from 2 to 3 tests:

| Substance | Effects on LV-dP/dtmax % increase | Effect on heart rate in beats per minute | pA2 inotropia | pA2 heart rate |
|---|---|---|---|---|
| A | +50 | −23 | 6.30 | 8.20 |
| B | +51 | −47 | 6.83 | 6.95 |
| C | +25 | −51 | 6.76 | 7.22 |
| D | +51 | −49 | 6.67 | 7.24 |
| E | +49 | −71 | 6.19 | 7.23 |
| F | +37 | −94 | 7.14 | 6.96 |
| G | +38 | −36 | 6.32 | 6.38 |
| H | +10 | −90 | 8.28 | >9.0 |
| I | +58 | −59 | 7.17 | 7.89 |
| K | +11 | −121 | 6.56 | 7.52 |
| L | +66 | −51 | 6.23 | 6.77 |
| M | +51 | −64 | 7.05 | 8.20 |
| N | +34 | −94 | 7.34 | 8.34 |
| O | +38 | −116 | 6.44 | 7.70 |
| P | +69 | −61 | 5.31 | 6.45 |

The compounds mentioned above show no negative inotropic effects up to a dosage of 4.4 mg/kg i.v., nor were any cardiac rhythm disorders observed. The new compounds are therefore well tolerated in therapeutic doses.

In view of their pharmacological properties the new compounds and the physiologically acceptable acid addition salts thereof are suitable for the treatment of myocardial ischaemia (angina), for treating cardiac insufficiency, for preventing the progression of cardiac insufficiency after myocardial infarct and for treating hypertension.

The dosage required to achieve such an effect will conveniently be 20 to 100 mg, preferably 30 to 75 mg, for intravenous administration, and 50 to 200 mg, preferably 75 to 150 mg, for oral administration, taken once or twice daily. For this purpose, the compounds prepared according to the invention, optionally combined with other active substances, may be formulated together with one or more inert conventional carriers and/or diluents, such as corn starch, lactose, glucose, microcrystalline cellulose, magnesium stearate, polyvinylpyrrolidone, citric acid, tartaric acid, water/glycerol, water/sorbitol, water/polyethylene glycol, propylene glycol, cetylstearyl alcohol, carboxymethyl cellulose or fatty substances such as hard fat or suitable mixtures thereof, into the usual galenic preparations such as plain or coated tablets, capsules, powders, suspensions or suppositories.

The Examples which follow are intended to illustrate the invention:

EXAMPLE I 1-(1-Naphthyloxy)-2,3-epoxypropane 14.1 g (100 mmol) of 1-naphthol and 11.2 g (100 mmol) of potassium tert.butoxide are dissolved at 50° C. in 50 ml of dimethylsulphoxide. Then, at ambient temperature, 15.0 g (110 mmol) of epibromohydrin are added dropwise, with stirring, and the mixture gradually warms up to about 50° C. After two hours, 200 ml of water are added and the mixture is extracted three times with 50 ml of ethyl acetate. The combined organic phases are washed with 100 ml of water, dried over sodium sulphate and evaporated down. The crude product thus obtained is purified by vacuum distillation (b.p.$_{0.1\ mm}$: 108°–110° C.).

Yield: 16.1 g (80% of theory).

The following epoxides are obtained analogously:

1-(4-aminocarbonylmethyl-phenoxy)-2,3-epoxypropane $R_F$ value: 0.68 (silica gel, dichloromethane/methanol=9:1).

Melting point: 172°–173° C.

(3,4-dihydroquinolin-2-on-5-yl)-2,3-epoxy-1-propylether $R_F$ value: 0.66 (silica gel, dichloromethane/methanol=9:1).

1-(2-allyloxy-phenoxy)-2,3-epoxypropane $R_F$ value: 0.88 (silica gel, dichloromethane).

1-(2-cyano-phenoxy)-2,3-epoxypropane $R_F$ value: 0.86 (silica gel, dichloromethane/methanol=9:1).

1-(2-chloro-5-methyl-phenoxy)-2,3-epoxypropane $R_F$ value: 0.85 (silica gel, dichloromethane).

1-(2-allyl-phenoxy)-2,3-epoxypropane $R_F$ value: 0.92 (silica gel, dichloromethane).

1-[4-(2-cyclobutylmethoxy-ethyl)phenoxy]-2,3-epoxypropane $R_F$ value: 0.43 (silica gel, dichloromethane/methanol=50:1).

1-[4-(2-isobutoxy-ethyl)phenoxy]-2,3-epoxypropane $R_F$ value: 0.62 (silica gel, dichloromethane/methanol=19:1).

1-[4-(2-cyclopropylmethoxy-ethyl)phenoxy]-2,3-epoxypropane $R_F$ value: 0.31 (silica gel, dichloromethane).

1-(4-methanesulphonyloxy-phenoxy)-2,3-epoxypropane $R_F$ value: 0.66 (silica gel, dichloromethane/ethanol=50:1).

1-(4-butanesulphonyloxy-phenoxy)-2,3-epoxypropane $R_F$ value: 0.42 (silica gel, dichloromethane/ethanol=50:1).

1-(4-isopropanesulphonyloxy-phenoxy)-2,3-epoxypropane $R_F$ value: 0.38 (silica gel, dichloromethane/ethanol=50:1).

1-(4-(2-isopropoxyethoxy)methyl-phenoxy)-2,3-epoxypropane $R_F$ value: 0.68 (silica gel, dichloromethane/ethanol=19:1).

1-[4-(2-phenoxyethoxymethyl)phenoxy]-2,3-epoxypropane $R_f$ value: 0.70 (silica gel, dichloromethane/ethanol = 19:1).

1-[4-(2-n-butyloxyethoxymethyl)phenoxy]-2,3-epoxypropane $R_f$ value: 0.69 (silica gel, dichloromethane/ethanol = 19:1).

1-[4-(2-methoxyethoxy-methyl)phenoxy]-2,3-epoxypropane $R_f$ value: 0.78 (silica gel, dichloromethane/methanol = 30:1).

EXAMPLE II

6-[4-(3-Phthalimidopropylsulphonyl)phenyl]-4,5-dihydro-3(2H)-pyridazinone 34 g (78.2 mmol) of methyl 4-oxo-4-[4-(3-phthalimidopropylsulphonyl)phenyl]butyrate are refluxed for two hours in a solution of 6 ml (120 mmol) of hydrazine hydrate (99%) in 350 ml of glacial acetic acid. Then the mixture is poured onto 2.5 liters of ice water, the product precipitated is suction filtered and dried in a circulating air dryer at 80° C.

Yield: 96.5% of theory.
Melting point: 205°–207° C.

EXAMPLE III

6-[1-(2-Acetylaminoethyl)benzimidazol-5-yl]-3(2H)-pyridazinone 14.2 g (49.4 mmol) of 6-(3-amino-4-acetylaminoethylaminophenyl)-3(2H)-pyridazinone are refluxed for one hour in 60 ml of formic acid. Then the excess formic acid is distilled off in vacuo, the residue is mixed with 50 ml of ice water and then adjusted to pH 8-9 with concentrated ammonia solution. The product precipitated is suction filtered, washed with about 50 ml of cold water, then with 50 ml of ether and dried.

Yield: 54% of theory.
Melting point: >250° C.

EXAMPLE IV

6-[1-(2-Acetaminoethyl)-2-hydroxy-benzimidazol-5-yl]-4,5-dihydro-3(2H)-pyridazinone To a solution of 580 mg (2.0 mmol) of 6-(3-amino-4-acetylaminoethylamino-phenyl)-4,5-dihydro-3(2H)-pyridazinone in 50 ml of dimethylformamide, 325 mg (2.0 mmol) of carbonyldiimidazole are added at 50° C. After 45 minutes at 50° C. the mixture is evaporated to dryness and the residue is mixed with 10 ml of water. The product precipitated is suction filtered, washed with 5 ml of water and dried.

Yield: 79% of theory.
Melting point: >250° C.

EXAMPLE V

6-[1-(2-Acetaminoethyl)benztriazol-5-yl]-4,5-dihydro-3(2H)-pyridazinone 15.98 g (55.3 mmol) of 6-(3-amino-4-acetaminoethylamino-phenyl)-4,5-dihydro-3(2H)-pyridazinone are dissolved in 300 ml of 2N sulphuric acid, then cooled to 2°–5° C. and a solution of 4.2 g (61 mmol) of sodium nitrite in 70 ml of water is slowly added dropwise with stirring. After about one hour the cooling bath is removed and the mixture is stirred for a further hour at ambient temperature. The solids precipitated are suction filtered, stirred into 100 ml of a 5% sodium bicarbonate solution and suction filtered again after 10 minutes.

Yield: 49% of theory.
Melting point: 255°–257° C.

EXAMPLE VI

5-Methyl-6-[2-(2-phthalimidoethyl)benzimidazol-5-yl]-4,5-dihydro-3(2H)-pyridazinone 120 g (286 mmol) of 5-methyl-6-[3-amino-4-(2-phthalimidopropionylamido)phenyl]-4,5-dihydro-3(2H)-pyridazinone are refluxed for one hour in 1.2 liters of glacial acetic acid. The mixture is then stirred into 1 liter of water and the impurities precipitated are filtered off. Then the filtrate is evaporated to dryness using a rotary evaporator and the solid residue is triturated with 200 ml of 2N ammonia solution. Then the solid material is suction filtered and recrystallised from methanol.

Yield: 71% of theory.
Melting point: 148°–150° C.

EXAMPLE VII

5-Methyl-6-[2-(4-aminobutylamino)benzoxazol-5-yl]-4,5-dihydro-3(2H)-pyridazinone 4.1 g (15.0 mmol) of 5-methyl-6-(2-methylthiobenzoxazol-5-yl)-4,5-dihydro-3(2H)-pyridazinone and 15 ml of 1,4-diaminobutane are heated to 60° C. for 45 minutes, then stirred into 200 ml of water and left to crystallise at ambient temperature. After about 30 minutes the product is suction filtered, washed with about 50 ml of water and dried at 60° C. in a circulating air dryer.

Yield: 89% of theory.
Melting point: 184°–187° C.

EXAMPLE VIII

6-[4-((2-tert.Butoxycarbonylamino)ethylaminocarbonylmethyl)-phenyl]-4,5-dihydro-3(2H)-pyridazinone 2.3 g (10.0 mmol) of 6-(4-carboxymethyl-phenyl)-4,5-dihydro-3(2H)-pyridazinone are dissolved in 30 ml of dimethylformamide, 1.8 g (11.0 mmol) of carbonyldiimidazole are added and the mixture is stirred for 30 minutes at ambient temperature. Then 1.2 g (7.3 mmol) of 2-tert.butoxycarbonylaminoethylamine are added and the mixture is stirred for a further hour. The reaction mixture is then stirred into about 1 liter of water and left to crystallise overnight. The product precipitated is suction filtered, washed with about 30 ml of water and dried in a circulating air dryer.

Yield: 52% of theory.
Melting point: 226°–228° C.

EXAMPLE IX

6-[4-((2-Aminoethyl)aminocarbonylmethyl)phenyl]-4,5-dihydro-3(2H)-pyridazinone

A mixture of 6.8 g (18 mmol) of 6-[4-((2-tert.butoxycarbonylaminoethyl)aminocarbonylmethyl)-phenyl]4,5-dihydro-3(2H)-pyridazinone, 25 ml of ethanol and 50 ml of 2N hydrochloric acid is refluxed for about 2 minutes, then the ethanol is distilled off, the aqueous solution is made alkaline with concentrated ammonia solution and finally the precipitate is suction filtered. This product is purified by chromatography on 200 g of silica gel (eluant: dichloromethane/methanol/ammonia = 70:30:1).

Yield: 69% of theory.
Melting point: 193°–196° C.

EXAMPLE X

6-[1-(2-Aminoethyl)benzimidazol-5-yl]-3(2H)-pyridazinone 8.0 g (26.0 mmol) of 6-[1-(2-acetylaminoethyl)benzimidazol-5-yl]-3(2H)-pyridazinone are refluxed for 4 hours in 80 ml of 5N sodium hydroxide solution. After cooling the mixture is adjusted to pH 8-9 with concentrated hydrochloric acid, the product precipitated is suction filtered and dried in a vacuum drying cupboard. The crude product obtained is used again without any further purification.

Yield: 99% of theory, amorphous.

EXAMPLE XI

6-[4-(3-Aminopropylsulphonyl)phenyl]-4,5-dihydro-3(2H)-pyridazinone 30.0 g (70.7 mmol) of 6-[4-(3-phthalimidopropylsulphonyl)phenyl]-4,5-dihydro-3(2H)-pyridazinone are stirred vigorously for two hours at ambient temperature in a mixture of 200 ml of toluene and 300 ml of 40% aqueous methylamine solution. Then the solid matter precipitated is suction filtered, washed successively with 100 ml of water, 50 ml of acetone and 50 ml of diethylether and then dried over phosphorus pentoxide in a vacuum drying cupboard.

Yield: 20.2 g (97% of theory).
Melting point: from 100° C. (decomp.).

EXAMPLE XII

6-[4-(2-Aminoethoxy)-3-methyl-phenyl]-3(2H)-pyridazinone

To a mixture of 24.7 g (0.1 mol) of 6-[4-(2-aminoethoxy)-3-methyl-phenyl]-4,5-dihydro-3(2H)-pyridazinone in 600 ml of glacial acetic acid and 9.8 g (0.1 mol) of concentrated sulphuric acid, 19.2 g (0.12 mol) of bromine dissolved in 20 ml of glacial acetic acid are slowly added dropwise, with stirring. After stirring for 1 hour at 70° C. the mixture is cooled, stirred for a further 12 hours at 20° C., then the yellow precipitate is suction filtered and washed with acetone. In order to liberate the base it is suspended in 500 ml of water and made alkaline with concentrated ammonia. The product precipitated is suction filtered and dried.

Yield: 20.5 g (84% of theory), amorphous.
$R_f$ value: 0.30 (silica gel, dichloromethane/ethanol=9:1).
$C_{13}H_{15}N_3O_2$ (245.28).

| Calculated: | C 63.66 | H 6.16 | N 17.13 |
|---|---|---|---|
| Found: | 63.83 | 6.01 | 17.05 |

EXAMPLE 1

6-[4-[2-[3-(4-(2-Cyclopropylmethoxyethyl)phenoxy)-2-hydroxypropylamino]ethoxy]phenyl]-3(2H)-pyridazinone A solution of 1.5 g (6 mmol) of 1-[4-(2-cyclopropylmethoxyethyl)phenoxy]-2,3-epoxypropane and 1.2 g (5 mmol) of 6-[4-(2-aminoethoxy)phenyl-3(2H)-pyridazinone in 100 ml of absolute ethanol is refluxed for seven hours. The mixture is then evaporated to dryness and the crude product thus obtained is purified by chromatography over 200 g of silica gel (dichloromethane/methanol=9:1).

Yield: 950 mg (39.6% of theory).
Melting point: 134°-135° C.
$C_{27}H_{33}N_3O_5$ (479.58).

| Calculated: | C 67.62 | H 6.94 | N 8.76 |
|---|---|---|---|
| Found: | 67.46 | 6.94 | 8.58 |

EXAMPLE 2

6-[4-[2-[3-(4-(2-Isopropoxyethoxymethyl)phenoxy)-2-hydroxypropylamino]ethoxy]phenyl]-3(2H)-pyridazinone Prepared analogously to Example 1 from 1-[4-(2-isopropoxyethoxymethyl)phenoxy]-2,3-epoxypropane and 6-[4-(2-aminoethoxy)-phenyl]-3(2H)-pyridazinone.

Melting point: 106°-108° C.
$C_{27}H_{35}N_3O_6$ (497.6).

| Calculated: | C 65.17 | H 7.09 | N 8.44 |
|---|---|---|---|
| Found: | 64.95 | 7.03 | 8.44 |

EXAMPLE 3

6-[4-[2-[3-(4-(2-Isobutoxy-ethyl)phenoxy)-2-hydroxypropylamino]ethoxy]-3-methyl-phenyl]-4,5-dihydro-3(2H)-pyridazinone Prepared analogously to Example 1 from 1-[4-(2-isobutoxy-ethyl)-phenoxy]-2,3-epoxypropane and 6-[4-(2-aminoethoxy)-3-methyl-phenyl]-4,5-dihydro-3(2H)-pyridazinone.

Yield: 24% of theory.
Melting point: 119°-120° C.
$C_{28}H_{39}N_3O_5$ (497.6).

| Calculated: | C 67.58 | H 7.90 | N 8.44 |
|---|---|---|---|
| Found: | 67.56 | 7.88 | 8.64 |

EXAMPLE 4

6-[4-[2-[3-(4-(2-Cyclopropylmethoxy-ethyl)phenoxy)-2-hydroxypropylamino]ethoxy]-3-methyl-phenyl]-4,5-dihydro-3(2H)-pyridazinone Prepared analogously to Example 1 from 1-[4-(2-cyclopropylmethoxyethyl)phenoxy]-2,3-epoxypropane and 6- [4-(2-aminoethoxy)-3-methyl-phenyl]-4,5-dihydro-3(2H)-pyridazinone.

Yield: 20% of theory.
Melting point: 98°-99° C.
$C_{28}H_{37}N_3O_5$ (495.6).

| Calculated: | C 67.86 | H 7.53 | N 8.48 |
|---|---|---|---|
| Found: | 67.83 | 7.61 | 8.55 |

EXAMPLE 5

6-[4-[2-[3-(4-(2-Isopropoxyethoxy-methyl)phenoxy)-2-hydroxypropylamino]ethoxy]-3-methyl-phenyl]-4,5-dihydro-3(2H)-pyridazinone Prepared analogously to Example 1 from 1-[4-(2-isopropoxyethoxymethyl)phenoxy]-2,3-epoxypropane and 6-[4-(2-aminoethoxy)-3-methyl-phenyl]-4,5-dihydro-3(2H)-pyridazinone.

Yield: 16% of theory.

Melting point: 95°–96° C.
$C_{28}H_{39}N_3O_6$ (513.6).

| Calculated: | C 65.48 | H 7.65 | N 8.18 |
|---|---|---|---|
| Found: | 65.31 | 7.75 | 8.24 |

EXAMPLE 6

6-[4-[3-[3-(4-(2-Cyclopropylmethoxy-ethyl)phenoxy)-2-hydroxypropylamino]propoxy]-3-methyl-phenyl]-4,5-dihydro-3(2H)-pyridazinone Prepared analogously to Example 1 from 1-[4-(2-cyclopropylmethoxyethyl)phenoxy]-2,3-epoxypropane and 6-[4-(3-aminopropoxy)-3-methyl-phenyl]-4,5-dihydro-3(2H)-pyridazinone.
Yield: 7% of theory.
Melting point: 142°–145° C.
$C_{29}H_{39}N_3O_5$ (509.6).

| Calculated: | C 68.35 | H 7.71 | N 8.24 |
|---|---|---|---|
| Found: | 68.13 | 7.62 | 8.10 |

EXAMPLE 7

6-[4-[3-[3-(4-(2-Cyclobutylmethoxy-ethyl)phenoxy)-2-hydroxypropylamino]propoxy]-3-methyl-phenyl]-4,5-dihydro-3(2H)-pyridazinone Prepared analogously to Example 1 from 1-[4-(2-cyclobutylmethoxyethyl)phenoxy]-2,3-epoxypropane and 6-[4-(3-aminopropoxy)-3-methyl-phenyl]-4,5-dihydro-3(2H)-pyridazinone.
Yield: 21% of theory.
Melting point: 149°–152° C.
$C_{30}H_{41}N_3O_5$ (523.7).

| Calculated: | C 68.81 | H 7.89 | N 8.02 |
|---|---|---|---|
| Found: | 68.72 | 7.71 | 7.73 |

EXAMPLE 8

6-[4-[3-[3-(4-(2-Isobutoxy-ethyl)phenoxy)-2-hydroxypropylamino]propoxy]-3-methyl-phenyl]-4,5-dihydro-3(2H)-pyridazinone Prepared analogously to Example 1 from 1-[4-(2-isobutoxy-ethyl)-phenoxy]-2,3-epoxypropane and 6-[4-(3-aminopropoxy)-3-methyl-phenyl]-4,5-dihydro-3(2H)-pyridazinone.
Yield: 18% of theory.
Melting point: 145°–147° C.
$C_{29}H_{41}N_3O_5$ (511.7).

| Calculated: | C 68.08 | H 8.08 | N 8.21 |
|---|---|---|---|
| Found: | 67.82 | 8.20 | 8.19 |

EXAMPLE 9

6-[4-[3-[3-(4-(2-Isopropoxyethoxy-methyl)phenoxy)-2-hydroxypropylamino]propoxy]-3-methyl-phenyl]-4,5-dihydro-3(2H)-pyridazinone Prepared analogously to Example 1 from 1-[4-(2-isopropoxyethoxymethyl)phenoxy]-2,3-epoxypropane and 6-4-(3-aminopropoxy)-3-methyl-phenyl]-4,5-dihydro-3(2H)-pyridazinone.
Yield: 21% of theory, amorphous.
$C_{29}H_{41}N_3O_6$ (527.7).

| Calculated: | C 66.01 | H 7.83 | N 7.96 |
|---|---|---|---|
| Found: | 65.88 | 7.89 | 7.78 |

$^1$H-NMR spectrum (CDCl$_3$/CD$_3$OD): δ=1.18 (d,6H); 2.13 (m,2H); 2.21 (s,3H); 2.56 (t,2H); 2.97 (m,6H); 3.60 (m,5H); 3.90–4.90 (m,5H); 4.50 (s,2H); 6.88 (m,3H); 7.27 (m,2H); 7.50 (m,2H) ppm.

EXAMPLE 10

6-[4-[3-[3-(4-(2-Cyclobutylmethoxy-ethyl)phenoxy)-2-hydroxypropylamino]propoxy]-3-chloro-phenyl]-4,5-dihydro-3(2H)-pyridazinone Prepared analogously to Example 1 from 1-[4-(2-cyclobutylmethoxy-ethyl)phenoxy]-2,3-epoxypropane and 6-[4-(3-aminopropoxy)-3-chloro-phenyl]-4,5-dihydro-3(2H)-pyridazinone.
Yield: 25% of theory.
Melting point: 120°–122° C.
$C_{29}H_{38}ClN_3O_5$ (544.1).

| Calculated: | C 64.02 | H 7.04 | N 7.72 | Cl 6.52 |
|---|---|---|---|---|
| Found: | 63.88 | 6.87 | 7.82 | 6.82 |

EXAMPLE 11

6-[4-[3-[3-(4-(2-Cyclopropylmethoxy-ethyl)phenoxy)-2-hydroxypropylamino]propoxy]-3-chloro-phenyl]-4,5-dihydro-3(2H)-pyridazinone Prepared analogously to Example 1 from 1-[4-(2-cyclopropylmethoxyethyl)phenoxy]-2,3-epoxypropane and 6-[4-(3-aminopropoxy)-3-chloro-phenyl]-4,5-dihydro-3(2H)-pyridazinone.
Yield: 33% of theory.
Melting point: 118°–120° C.
$C_{28}H_{36}ClN_3O_5$ (530.1).

| Calculated: | C 63.44 | H 6.85 | N 7.93 | Cl 6.69 |
|---|---|---|---|---|
| Found: | 63.34 | 6.83 | 7.95 | 6.91 |

EXAMPLE 12

6-[4-[3-[3-(4-(2-Isopropoxyethoxy-methyl)phenoxy)-2-hydroxypropylamino]propoxy]-3-chloro-phenyl]-4,5-dihydro-3(2H)-pyridazinone Prepared analogously to Example 1 from 1-[4-(2-isopropoxyethoxymethyl)phenoxy]-2,3-epoxypropane and 6-[4-(3-aminopropoxy)-3-chloro-phenyl]-4,5-dihydro-3(2H)-pyridazinone.
Yield: 15% of theory.
Melting point: 187°–189° C.
$C_{28}H_{38}ClN_3O_6 \times HCL$ (584.6).

| Calculated: | C 57.52 | H 6.72 | N 7.19 | Cl 12.13 |
|---|---|---|---|---|
| Found: | 57.44 | 6.59 | 7.14 | 12.16 |

EXAMPLE 13

6-[4-[2-[3-(4-(2-Cyclobutylmethoxy-ethyl)phenoxy)-2-hydroxypropylamino]ethoxy]-3-chloro-phenyl]-4,5-dihydro-3(2H)-pyridazinone Prepared analogously to Example 1 from 1-[4-(2-cyclobutylmethoxyethyl)phenoxy]-2,3-epoxypropane and 6-[4-(2-aminoethoxy)-3-chloro-phenyl]-4,5-dihydro-3(2H)-pyridazinone.
Yield: 27% of theory.
Melting point: 128°–130° C.
$C_{28}H_{36}ClN_3O_5$ (530.1).

| Calculated: | C 63.44 | H 6.85 | N 7.93 | Cl 6.69 |
|---|---|---|---|---|
| Found: | 63.52 | 6.71 | 8.02 | 6.89 |

EXAMPLE 14

6-[4-[2-[3-(4-(2-Isobutoxy-ethyl)phenoxy)-2-hydroxypropylamino]ethoxy]-3-chloro-phenyl]-4,5-dihydro-3(2H)-pyridazinone Prepared analogously to Example 1 from 1-[4-(2-isobutoxy-ethyl)-phenoxy]-2,3-epoxypropane and 6-[4-(2-aminoethoxy)-3-chloro-phenyl]-4,5-dihydro-3(2H)-pyridazinone.
Yield: 33% of theory.
Melting point: 127°–129° C.
$C_{27}H_{36}ClN_3O_5$ (518.1).

| Calculated: | C 62.59 | H 7.00 | N 8.11 | Cl 6.84 |
|---|---|---|---|---|
| Found: | 62.46 | 7.02 | 8.14 | 7.06 |

EXAMPLE 15

6-[4-[2-[3-(4-(2-Isopropoxyethoxy-methyl)phenoxy)-2-hydroxypropylamino]ethoxy]-3-chloro-phenyl]-4,5-dihydro-3(2H)-pyridazinone Prepared analogously to Example 1 from 1-[4-(2-isopropoxyethoxymethyl)phenoxy]-2,3-epoxypropane and 6-[4-(2-aminoethoxy)-3-chloro-phenyl]-4,5-dihydro-3(2H)-pyridazinone.
Yield: 19% of theory.
Melting point: 96°–99° C.
$C_{27}H_{36}ClN_3O_6$ (534.1).

| Calculated: | C 60.71 | H 6.79 | N 7.87 | Cl 6.64 |
|---|---|---|---|---|
| Found: | 60.59 | 6.90 | 8.10 | 6.45 |

EXAMPLE 16

6-[4-[2-[3-(Naphthyl-1-oxy)-2-hydroxypropylamino]ethoxy]phenyl]-4,5-dihydro-5-methyl-3(2H)-pyridazinone Prepared analogously to Example 1 from 1-(naphthyl-1-oxy)-2,3-epoxypropane and 6-[4-(2-aminoethoxy)-phenyl]-4,5-dihydro-5-methyl-3(2H)-pyridazinone.
Yield: 34% of theory, amorphous.
$C_{26}H_{29}N_3O_4$ (447.5).

| Calculated: | C 69.78 | H 6.53 | N 9.39 |
|---|---|---|---|
| Found: | 69.54 | 6.44 | 9.35 |

$^1$H-NMR spectrum (CDCl$_3$/CD$_3$OD): δ=1.22 (d,3H); 2.42 (dd,1H); 2.71 (dd,1H); 2.9–3.2 (m,4H); 3.3–3.45 (m,1H); 4.1–4.4 (m,6H); 6.8–7.0 (m,3H); 7.3–7.6 (m,4H); 7.65–7.85 (m,3H); 8.25 (m,1H) ppm.

EXAMPLE 17

6-[4-[2-[3-(2-Chloro-5-methyl-phenoxy)-2-hydroxypropylamino]ethoxy]phenyl]-4,5-dihydro-5-methyl-3(2H)-pyridazinone Prepared analogously to Example 1 from 1-(2-chloro-5-methylphenoxy)-2,3-epoxypropane and 6-[4-(2-aminoethoxy)phenyl]-4,5-dihydro-5-methyl-3(2H)-pyridazinone.
Yield: 37% of theory, amorphous.
$C_{23}H_{28}ClN_3O_4$ (445.9).

| Calculated: | C 61.95 | H 6.33 | N 9.42 | Cl 7.95 |
|---|---|---|---|---|
| Found: | 61.84 | 6.39 | 9.45 | 7.96 |

$^1$H-NMR spectrum (CDCl$_3$/CD$_3$OD): δ=1.22 (d,3H); 2.31 (s,3H); 2.40 (dd,1H); 2.70 (dd, 1H); 2.85–3.20 (m,4H); 3.86 (m,1H); 3.95–4.20 (m,5H); 6.75 (m,2H); 6.95 (d,2H); 7.20 (d,1H); 7.70 (d,2H) ppm.

EXAMPLE 18

6-[4-[2-[3-(2-Cyano-phenoxy)-2-hydroxypropylamino]ethoxy]phenyl]-4,5-dihydro-5-methyl-3(2H)-pyridazinone Prepared analogously to Example 1 from 1-(2-cyano-phenoxy)-2,3-epoxypropane and 6-[4-(2-aminoethoxy)-phenyl]-4,5-dihydro-5-methyl-3(2H)-pyridazinone.
Yield: 23% of theory, amorphous.
$C_{23}H_{26}N_4O_4$ (422.5).

| Calculated: | C 65.39 | H 6.20 | N 13.26 |
|---|---|---|---|
| Found: | 65.28 | 6.32 | 13.13 |

$^1$H-NMR spectrum (CDCl$_3$/CD$_3$OD): δ=1.22 (d,3H); 2.42 (dd,1H); 2.72 (dd,1H); 2.85–3.15 (m,4H); 3.37 (m,1H); 4.05–4.25 (m,5H); 6.90–7.10 (m,4H); 7.90–7.80 (m,4H) ppm.

EXAMPLE 19

6-[4-[2-[3-(2-Allyloxy-phenoxy)-2-hydroxypropylamino]ethoxy]phenyl]-4,5-dihydro-5-methyl-3(2H)-pyridazinone Prepared analogously to Example 1 from 1-(2-allyloxy-phenoxy)-2,3-epoxypropane and 6-[4-(2-aminoethoxy)phenyl]-4,5-dihydro-5-methyl-3(2H)-pyridazinone.
Yield: 39% of theory, amorphous.
$C_{25}H_{31}N_3O_5$ (453.5).

| Calculated: | C 66.21 | H 6.89 | N 9.26 |
|---|---|---|---|
| Found: | 65.92 | 7.00 | 9.17 |

$^1$H-NMR spectrum (CDCl$_3$/CD$_3$OD): δ=1.22 (d,3H); 2.42 (dd,1H); 2.72 (dd,1H); 2.90 (m,2H); 3.10 (t,2H); 3.38 (m,1H); 3.95–4.20 (m,5H); 4.60 (m,2H) 5.25–5.50 (m,2H); 6.10 (m,1H); 6.90–7.00 (m,6H); 7.70 (d,2H) ppm.

EXAMPLE 20

6-[4-[2-[3-(3,4-Dihydro-2-hydroxy-quinolin-5-yloxy)-2-hydroxypropylamino]ethoxy]phenyl]-4,5-dihydro-5-methyl-3(2H)-pyridazinone Prepared analogously to Example 1 from 1-(3,4-dihydro-2-hydroxy-quinolin-5-yloxy)-2,3-epoxypropane and 6-[4-(2-aminoethoxy)phenyl]-4,5-dihydro-5-methyl-3(2H)-pyridazinone.
Yield: 32% of theory, amorphous.
$C_{25}H_{30}N_4O_5$ (466.5).

| Calculated: | C 64.36 | H 6.48 | N 12.01 |
|---|---|---|---|
| Found: | 64.12 | 6.61 | 11.85 |

$^1$H-NMR spectrum (CDCl$_3$/CD$_3$OD): δ=1.23 (d,3H); 2.38–3.40 (m,11H); 3.95–4.20 (m,5H); 6.48 (d,1H); 6.60 (d,1H); 6.93 (d,2H); 7.11 (t,1H); 7.70 (d,2H) ppm.

EXAMPLE 21

6-[4-[2-[3-(4-(2-Cyclobutylmethoxy-ethyl)phenoxy)-2-hydroxypropylamino]ethoxy]phenyl]-4,5-dihydro-3(2H)-pyridazinone Prepared analogously to Example 1 from 1-[4-(2-cyclobutylmethoxyethyl)phenoxy]-2,3-epoxypropane and 6-[4-(2-aminoethoxy)-phenyl]-4,5-dihydro-3(2H)-pyridazinone.
Yield: 27% of theory.
Melting point: 116°–117° C.
$C_{28}H_{37}N_3O_5$ (495.6).

| Calculated: | C 67.86 | H 7.53 | N 8.48 |
|---|---|---|---|
| Found: | 67.69 | 7.51 | 8.44 |

EXAMPLE 22

6-[4-[2-[3-(4-((2-Isopropoxyethoxy)methyl)phenoxy)-2-hydroxypropylamino]ethoxy]phenyl]-4,5-dihydro-3(2H)-pyridazinone Prepared analogously to Example 1 from 1-[4-((2-isopropoxyethoxy)methyl)phenoxy]-2,3-epoxypropane and 6-[4-(2-aminoethoxy)-phenyl]-4,5-dihydro-3(2H)-pyridazinone.
Yield: 25% of theory.
Melting point: 102°–105° C.
$C_{27}H_{37}N_3O_6$ (499.6).

| Calculated: | C 64.91 | H 7.46 | N 8.41 |
|---|---|---|---|
| Found: | 64.89 | 7.64 | 8.46 |

EXAMPLE 23

6-[4-[2-[3-(4-(2-Cyclopropylmethoxy-ethyl)phenoxy)-2-hydroxypropylamino]ethoxy]phenyl]-4,5-dihydro-3(2H)-pyridazinone Prepared analogously to Example 1 from 1-[4-(2-cyclopropylmethoxy-ethyl)phenoxy]-2,3-epoxypropane and 6-[4-(2-aminoethoxy)-phenyl]-4,5-dihydro-3(2H)-pyridazinone.
Yield: 37% of theory.
Melting point: 121°–122° C.
$C_{27}H_{35}N_3O_5$ (481.6).

| Calculated: | C 67.34 | H 7.33 | N 8.73 |
|---|---|---|---|
| Found: | 67.13 | 7.34 | 8.59 |

EXAMPLE 24

6-[4-[3-[3-(4-(2-Cyclopropylmethoxy-ethyl)phenoxy)-2-hydroxypropylamino]propoxy]phenyl]-4,5-dihydro-3(2H)-pyridazinone Prepared analogously to Example 1 from 1-[4-(2-cyclopropylmethoxy-ethyl)phenoxy]-2,3-epoxypropane and 6-[4-(3-aminopropoxy)phenyl]-4,5-dihydro-3(2H)-pyridazinone.
Yield: 19% of theory.
Melting point: from 113° C. (sintering).
$C_{28}H_{37}N_3O_5$ (495.6).

| Calculated: | C 67.86 | H 7.53 | N 8.48 |
|---|---|---|---|
| Found: | 67.85 | 7.44 | 8.29 |

EXAMPLE 25

6-[3-[2-[3-(Naphthyl-1-oxy)-2-hydroxypropylamino]ethoxy]phenyl]-4,5-dihydro-5-methyl-3(2H)-pyridazinone Prepared analogously to Example 1 from 1-(naphthyl-1-oxy)-2,3-epoxypropane and 6-[3-(2-aminoethoxy)-phenyl]-4,5-dihydro-5-methyl-3(2H)-pyridazinone.
Yield: 36% of theory, amorphous.
$C_{26}H_{29}N_3O_4$ (447.5).

| Calculated: | C 69.78 | H 6.53 | N 9.39 |
|---|---|---|---|
| Found: | 69.58 | 6.55 | 9.33 |

$^1$H-NMR spectrum (CDCl$_3$/CD$_3$OD): δ=1.22 (d,3H); 2.42 (dd,1H); 2.70 (dd,1H); 2.90–3.40 (m,5H); 4.00–4.35 (m,5H); 6.85 (dd,1H); 6.98 (m,1H); 7.30–7.55 (m,7H); 7.80 (dd,1H); 8.35 (dd,1H) ppm.

EXAMPLE 26

6-[3-[2-[3-(2-Cyano-phenoxy)-2-hydroxypropylamino]ethoxy]phenyl]-4,5-dihydro-5-methyl-3(2H)-pyridazinone Prepared analogously to Example 1 from 1-(2-cyano-phenoxy)-2,3-epoxypropane and 6-[3-(2-aminoethoxy)-phenyl]-4,5-dihydro-5-methyl-3(2H)-pyridazinone.
Yield: 27% of theory, amorphous.
$C_{23}H_{26}N_4O_4$ (422.5).

| Calculated: | C 65.39 | H 6.20 | N 13.26 |
|---|---|---|---|
| Found: | 65.12 | 6.11 | 13.09 |

$^1$H-NMR spectrum (CDCl$_3$/CD$_3$OD): δ=1.24 (d,3H); 2.40–3.40 (m,7H); 4.05–4.55 (m,5H); 7.00 (m,3H); 7.25–7.40 (m,3H); 7.45–7.60 (m,2H) ppm.

EXAMPLE 27

6-[3-[2-[3-(3,4-Dihydro-2-hydroxy-quinolin-5-yloxy)-2-hydroxypropylamino]ethoxy]phenyl]-4,5-dihydro-5-methyl-3(2H)-pyridazinone Prepared analogously to Example 1 from 1-(3,4-dihydro-2-hydroxy-quinolin-5-yloxy)-2,3-epoxypropane and 6-[3-(2-aminoethoxy)phenyl]-4,5-dihydro-5-methyl-3(2H)-pyridazinone.

Yield: 43% of theory, amorphous.
$C_{25}H_{30}N_4O_5$ (466.5).

| Calculated: | C 64.36 | H 6.48 | N 12.01 |
| --- | --- | --- | --- |
| Found: | 64.35 | 6.57 | 11.78 |

$^1$H-NMR spectrum (CDCl$_3$/CD$_3$OD): δ=1.22 (d,3H); 2.40–3.40 (m,10H); 3.95–4.20 (m,5H); 6.50 (d,1H); 6.60 (d,1H); 6.98 (m,1H); 7.11 (t,1H); 7.30–7.42 (m,3H) ppm.

EXAMPLE 28

6-[3-[2-[3-(2-Chloro-5-methyl-phenoxy)-2-hydroxypropylamino]ethoxy]phenyl]-4,5-dihydro-5-methyl-3(2H)-pyridazinone Prepared analogously to Example 1 from 1-(2-chloro-5-methyl-phenoxy)-2,3-epoxypropane and 6-[3-(2-aminoethoxy)phenyl]-4,5-dihydro-5-methyl-3(2H)-pyridazinone.

Yield: 22% of theory, amorphous.
$C_{23}H_{28}ClN_3O_4$ (445.9)

| Calculated: | C 61.95 | H 6.33 | N 9.42 | Cl 7.95 |
| --- | --- | --- | --- | --- |
| Found: | 61.78 | 6.21 | 9.33 | 8.03 |

$^1$H-NMR spectrum (CDCl$_3$/CD$_3$OD): δ=1.22 (d,3H); 2.31 (s,3H); 2.35–3.40 (m,7H); 4.00–4.25 (m,5H); 6.75 (m,2H); 6.99 (m,1H); 7.20 (d,1H); 7.33 (m,3H) ppm.

EXAMPLE 29

6-[3-[2-[3-(2-Allyloxy-phenoxy)-2-hydroxypropylamino]ethoxy]phenyl]-4,5-dihydro-5-methyl-3(2H)-pyridazinone Prepared analogously to Example 1 from 1-(2-allyloxy-phenoxy)-2,3-epoxypropane and 6-[3-(2-aminoethoxy)phenyl]-4,5-dihydro-5-methyl-3(2H)-pyridazinone.

Yield: 33% of theory, amorphous.
$C_{25}N_{31}N_3O_5$ (453.5).

| Calculated: | C 66.21 | H 6.89 | N 9.26 |
| --- | --- | --- | --- |
| Found: | 66.05 | 6.98 | 9.11 |

$^1$H-NMR spectrum (CDCl$_3$/CD$_3$OD): δ=1.22 (d,3H); 2.35–3.40 (m,7H); 3.95–4.20 (m,5H); 4.56 (m,2H); 5.20–5.50 (m,2H); 5.95–6.20 (m,1H); 6.80–7.00 (m,5H); 7.20–7.40 (m,3H) ppm.

EXAMPLE 30

6-[3-[2-[3-(4-(2-Cyclopropylmethoxy-ethyl)phenoxy)-2-hydroxypropylamino]ethoxy]phenyl]-4,5-dihydro-3(2H)-pyridazinone Prepared analogously to Example 1 from 1-[4-(2-cyclopropylmethoxy-ethyl)phenoxy]-2,3-epoxypropane and 6-[3-(2-aminoethoxy)phenyl]-4,5-dihydro-3(2H)-pyridazinone.

Yield: 25% of theory.
Melting point: 102°–104° C.
$C_{27}H_{35}N_3O_5$ (481.6).

| Calculated: | C 67.34 | H 7.33 | N 8.73 |
| --- | --- | --- | --- |
| Found: | 67.15 | 7.21 | 8.77 |

EXAMPLE 31

6-[3-[2-[3-(4-(2-Isobutoxy-ethyl)phenoxy)-2-hydroxypropylamino]ethoxy]phenyl]-4,5-dihydro-3(2H)-pyridazinone Prepared analogously to Example 1 from 1-[4-(2-isobutoxy-ethyl)phenoxy]-2,3-epoxypropane and 6-[3-(2-aminoethoxy)phenyl]-4,5-dihydro-3(2H)-pyridazinone.

Yield: 14% of theory.
Melting point: 109°–110° C.
$C_{27}H_{37}N_3O_5$ (483.6).

| Calculated: | C 67.06 | H 7.71 | N 8.69 |
| --- | --- | --- | --- |
| Found: | 66.86 | 7.54 | 8.64 |

EXAMPLE 32

6-[3-[2-[3-(4-(2-Cyclobutylmethoxy-ethyl)phenoxy)-2-hydroxypropylamino]ethoxy]phenyl]-4,5-dihydro-3(2H)-pyridazinone Prepared analogously to Example 1 from 1-[4-(2-cyclobutylmethoxyethyl)phenoxy]-2,3-epoxypropane and 6-[3-(2-aminoethoxy)phenyl]-4,5-dihydro-3(2H)-pyridazinone.

Yield: 19% of theory.
Melting point: 102°–103° C.
$C_{28}H_{37}N_3O_5$ (495.6).

| Calculated: | C 67.86 | H 7.53 | N 8.48 |
| --- | --- | --- | --- |
| Found: | 67.60 | 7.38 | 8.32 |

EXAMPLE 33

6-[3-[3-[3-(4-(2-Cyclopropylmethoxy-ethyl)phenoxy)-2-hydroxypropylamino]propoxy]phenyl]-4,5-dihydro-3(2H)-pyridazinone Prepared analogously to Example 1 from 1-[4-(2-cyclopropylmethoxyethyl)phenoxy]-2,3-epoxypropane and 6-[3-(3-aminopropoxy)phenyl]-4,5-dihydro-3(2H)-pyridazinone.

Yield: 12% of theory.
Melting point: 182°–183° C.
$C_{28}H_{37}N_3O_5$ (495.6).

| Calculated: | C 67.86 | H 7.53 | N 8.48 |
| --- | --- | --- | --- |
| Found: | 67.57 | 7.49 | 8.40 |

EXAMPLE 34

6-[2-[4-[3-(2-Cyano-phenoxy)-2-hydroxypropylamino]butylamino]benzoxazol-5-yl]-4,5-dihydro-5-methyl-3(2H)-pyridazinone Prepared analogously to Example 1 from 1-(2-cyano-phenoxy)-2,3-epoxypropane and 6-[2-(4-aminobutylamino)benzoxazol-5-yl]-4,5-dihydro-5-methyl-3(2H)-pyridazinone.

Yield: 42% of theory, amorphous.
$C_{26}H_{30}N_6O_4$ (490.6).

| Calculated: | C 63.65 | H 6.16 | N 17.13 |
|---|---|---|---|
| Found: | 63.76 | 6.18 | 16.98 |

$^1$H-NMR spectrum (CDCl$_3$/CD$_3$OD): δ=1.25 (d,3H); 1.60–1.90 (m,4H); 2.45 (dd,1H); 2.65–3.10 (m,7H); 3.30–3.60 (m,3H); 4.05–4.30 (m,3H); 6.45–7.30 (m,3H); 7.40–7.60 (m,3H); 7.76 (s,1H) ppm.

EXAMPLE 35

6-[2-[4-[3-(Naphthyl-1-oxy)-2-hydroxypropylamino]-butylamino]benzoxazol-5-yl]-4,5-dihydro-5-methyl-3(2H)-pyridazinone Prepared analogously to Example 1 from 1-(naphthyl-1-oxy)-2,3-epoxypropane and 6-[2-(4-aminobutylamino)benzoxazol-5-yl]-4,5-dihydro-5-methyl-3(2H)-pyridazinone.

Yield: 41% of theory, amorphous.
C$_{29}$H$_{33}$N$_5$O$_4$ (515.6).

| Calculated: | C 67.55 | H 6.45 | N 13.58 |
|---|---|---|---|
| Found: | 67.42 | 6.22 | 13.33 |

δ=1.22 (d,3H); 1.62–1.40 (m,4H); 2.40 (dd,1H); 2.60–3.10 (m,5H); 3.31 (m,1H); 3.49 (t,2H); 4.12–4.40 (m,3H); 6.82 (dd,1H); 7.17–7.53 (m,6H); 7.70–7.84 (m,2H); 8.23 (dd,1H) ppm.

EXAMPLE 36

6-[2-[3-[3-(2-Cyano-phenoxy)-2-hydroxypropylamino]-propylamino]benzoxazol-5-yl]-4,5-dihydro-5-methyl-3(2H)-pyridazinone Prepared analogously to Example 1 from 1-(2-cyano-phenoxy)-2,3-epoxypropane and 6-[2-(3-aminopropylamino)benzoxazol-5-yl]-4,5-dihydro-5-methyl-3(2H)-pyridazinone.

Yield: 47% of theory, amorphous.
C$_{25}$H$_{28}$N$_6$O$_4$ (476.5).

| Calculated: | C 63.01 | H 5.92 | N 17.64 |
|---|---|---|---|
| Found: | 62.89 | 5.81 | 17.49 |

$^1$H-NMR spectrum (CDCl$_3$/CD$_3$OD): δ=1.24 (d,3H); 1.84–2.00 (m,2H); 2.45 (dd,1H); 2.65–3.05 (m,7H); 3.38 (m,1H); 3.66 (t,2H); 4.10–4.30 (m,3H); 7.00 (m,2H); 7.20 (d,1H); 7.38–7.60 (m,3H); 7.88 (s,1H) ppm.

EXAMPLE 37

6-[2-[3-[3-(Naphthyl-1-oxy)-2-hydroxypropylamino]-propylamino]benzoxazol-5-yl]-4,5-dihydro-5-methyl-3(2H)-pyridazinone Prepared analogously to Example 1 from 1-(naphthyl-1-oxy)-2,3-epoxypropane and 6-[2-(3-aminopropylamino)benzoxazol-5-yl]-4,5-dihydro-5-methyl-3(2H)-pyridazinone.

Yield: 22% of theory, amorphous.
C$_{28}$H$_{31}$N$_5$O$_4$ (501.6).

| Calculated: | C 67.05 | H 6.23 | N 13.96 |
|---|---|---|---|
| Found: | 66.91 | 6.11 | 14.12 |

$^1$H-NMR spectrum (CDCl$_3$/CD$_3$OD): δ=1.24 (d,3H); 1.92 (m,2H); 2.40 (dd,1H); 2.62–3.05 (m,5H); 3.36 (m,1H); 3.55 (t,2H); 4.10–4.40 (m,3H); 6.85 (dd,1H); 7.18–7.53 (m,6H); 7.80 (m,2H); 8.20 (dd,1H) ppm.

EXAMPLE 38

6-[2-[2-[3-(2-Cyano-phenoxy)-2-hydroxypropylamino]ethyl]benzimidazol-5-yl]-4,5-dihydro-3(2H)-pyridazinone Prepared analogously to Example 1 from 1-(2-cyano-phenoxy)-2,3-epoxypropane and 6-[2-(2-aminoethyl)-benzimidazol-5-yl]-4,5-dihydro-3(2H)-pyridazinone.

Yield: 18% of theory.
Melting point: 183°–184° C.
C$_{23}$H$_{24}$N$_6$O$_3$ (432.5).

| Calculated: | C 63.88 | H 5.59 | N 19.43 |
|---|---|---|---|
| Found: | 63.70 | 5.45 | 19.40 |

EXAMPLE 39

6-[2-[2-[3-(Naphthyl-1-oxy)-2-hydroxypropylamino]ethyl]-benzimidazol-5-yl]-4,5-dihydro-3(2H)-pyridazinone Prepared analogously to Example 1 from 1-(naphthyl-1-oxy)-2,3-epoxypropane and 6-[2-(2-aminoethyl)-benzimidazol-5-yl]-4,5-dihydro-3(2H)-pyridazinone.

Yield: 22% of theory.
Melting point: 203°–204° C.
C$_{26}$H$_{27}$N$_5$O$_3$ (457.5).

| Calculated: | C 68.25 | H 5.95 | N 15.31 |
|---|---|---|---|
| Found: | 68.10 | 5.88 | 15.48 |

EXAMPLE 40

6-[2-[2-[3-(2-Chloro-5-methyl-phenoxy)-2-hydroxypropylamino]ethyl]benzimidazol-5-yl]-4,5-dihydro-3(2H)-pyridazinone Prepared analogously to Example 1 from 1-(2-chloro-5-methyl-phenoxy)-2,3-epoxypropane and 6-[2-(2-aminoethyl)benzimidazol-5-yl]-4,5-dihydro-3(2H)-pyridazinone.

Yield: 20% of theory.
Melting point: 182°–183° C.
C$_{23}$H$_{26}$ClN$_5$O$_3$ (455.9).

| Calculated: | C 60.59 | H 5.75 | N 15.36 | Cl 7.78 |
|---|---|---|---|---|
| Found: | 60.49 | 5.75 | 15.62 | 8.03 |

EXAMPLE 41

6-[2-[2-[3-(2-Allyloxy-phenoxy)-2-hydroxypropylamino]ethyl]benzimidazol-5-yl]-4,5-dihydro-3(2H)-pyridazinone Prepared analogously to Example 1 from 1-(2-allyloxy-phenoxy)-2,3-epoxypropane and 6-[2-(2-aminoethyl)benzimidazol-5-yl]-4,5-dihydro-3(2H)-pyridazinone.

Yield: 9% of theory.
Melting point: 172°–173° C.
C$_{25}$H$_{29}$N$_5$O$_4$ (463.5).

| Calculated: | C 64.78 | H 6.31 | N 15.11 |
|---|---|---|---|

| Found: | 64.72 | 6.38 | 15.20 |

EXAMPLE 42

6-[2-[2-[3-(4-(2-Isobutoxy-ethyl)phenoxy)-2-hydroxypropylamino]ethyl]benzimidazol-5-yl]-4,5-dihydro-3(2H)-pyridazinone Prepared analogously to Example 1 from 1-(4-[2-isobutoxy-ethyl)phenoxy]-2,3-epoxypropane and 6-[2-(2-aminoethyl)benzimidazol-5-yl]-4,5-dihydro-3(2H)-pyridazinone.

Yield: 9% of theory, amorphous. R$_f$ value: 0.47 (silica gel, dichloromethane/methanol/ammonia=80:20:0.5).

C$_{28}$H$_{37}$N$_5$O$_4$ (507.6).

| Calculated: | C 66.25 | H 7.35 | N 13.80 |
| Found: | 65.92 | 7.19 | 13.99 |

EXAMPLE 43

6-[2-[2-[3-(Naphthyl-1-oxy)-2-hydroxypropylamino]ethyl]benzimidazol-5-yl]-4,5-dihydro-5-methyl-3(2H)-pyridazinone Prepared analogously to Example 1 from 1-(naphthyl-1-oxy)-2,3-epoxypropane and 6-[2-(2-aminoethyl)-benzimidazol-5-yl]-4,5-dihydro-5-methyl-3(2H)-pyridazinone.

Yield: 30% of theory, amorphous.

C$_{27}$H$_{29}$N$_5$O$_3$ (471.6).

| Calculated: | C 68.77 | H 6.20 | N 14.85 |
| Found: | 68.57 | 6.18 | 14.64 |

$^1$H-NMR spectrum (d$_6$-DMSO/CD$_3$OD): δ=1.13 (d,3H); 2.28 (dd,1H); 2.65–3.20 (m,7H); 3.47 (m,1H); 4.05–4.20 (m,3H); 6.91 (dd,1H); 7.35–7.56 (m,5H); 7.70 (dd,1H); 7.80–7.90 (m,2H); 8.27 (m,1H) ppm.

EXAMPLE 44

6-[2-[2-[3-(4-Aminocarbonylmethyl-phenoxy)-2hydroxypropylamino]-ethyl]benzimidazol-5-yl]-4,5-dihydro-5-methyl-3(2H)-pyridazinone Prepared analogously to Example 1 from 1-(4-aminocarbonylmethylphenoxy)-2,3-epoxypropane and 6-[2-(2-aminoethyl)benzimidazol-5-yl]-4,5-dihydro-5-methyl-(3(2H)-pyridazinone.

Yield: 12% of theory, amorphous.

C$_{25}$H$_{30}$N$_6$O$_4$ (478.6).

| Calculated: | C 62.75 | H 6.32 | N 17.56 |
| Found: | 62.73 | 6.23 | 17.33 |

$^1$H-NMR spectrum (d$_6$-DMSO/CD$_3$OD): δ=1.14 (d,3H); 2.28 (dd,1H); 2.60–2.83 (m,3H); 3.02 (m,4H); 3.30 (m,2H); 3.48 (m,1H); 3.80–4.00 (m,3H); 6.84 (d,2H); 7.18 (m,2H); 7.50 (d,1H); 7.69 (dd,1H); 7.89 (d,1H) ppm.

EXAMPLE 45

6-[2-[2-[3-(3,4-Dihydro-2-hydroxy-quinolin-5-yloxy)-2-hydroxypropylamino]-ethyl]benzimidazol-5-yl]-4,5-dihydro-5-methyl-3(2H)-pyridazinone Prepared analogously to Example 1 from 1-(3,4-dihydro-2-hydroxy-quinolin-5-yloxy)-2,3-epoxypropane and 6-[2-(2-aminoethyl)benzimidazol-5-yl]-4,5-dihydro-5-methyl-3(2H)-pyridazinone.

Yield: 19% of theory.

Melting point: from 130° C. (sintering).

C$_{26}$H$_{30}$N$_6$O$_4$ (490.6).

| Calculated: | C 63.66 | H 6.16 | N 17.13 |
| Found: | 63.49 | 6.29 | 16.82 |

EXAMPLE 46

6-[2-[2-[3-(2-Allyloxy-phenoxy)-2-hydroxypropylamino]ethyl]benzimidazol-5-yl]-4,5-dihydro-5-methyl-3(2H)-pyridazinone Prepared analogously to Example 1 from 1-(2-allyloxy-phenoxy)-2,3-epoxypropane and 6-[2-(2-aminoethyl)benzimidazol-5-yl]-4,5-dihydro-5-methyl-3(2H)-pyridazinone.

Yield: 39% of theory, amorphous.

C$_{26}$H$_{31}$N$_5$O$_4$ (477.6).

| Calculated: | C 65.39 | H 6.54 | N 14.66 |
| Found: | 65.21 | 6.66 | 14.66 |

$^1$H-NMR spectrum (CDCl$_3$/CD$_3$OD): δ=1.27 (d,3H); 2.46 (dd,1H); 2.70–3.20 (m,8H); 3.48 (m,1H); 4.00 (m,2H); 4.18 (m,2H); 4.58 (dt,2H); 5.25–5.47 (m,2H); 5.95–6.16 (m,1H); 6.92 (s,4H); 7.50 (m,1H); 7.71 (dd,1H); 7.89 (d,1H) ppm.

EXAMPLE 47

6-[2-[2-[3-(4-(2-Cyclobutylmethoxy-ethyl)phenoxy)-2-hydroxypropylamino]ethyl]benzimidazol-5-yl]-4,5-dihydro-5-methyl-3(2H-pyridazinone-dihydrochloride Prepared analogously to Example 1 from 1-[4-(2-cyclobutylmethoxyethyl)phenoxy]-2,3-epoxypropane and 6-[2-(2-aminoethyl)benzimidazol-5-yl]-4,5-dihydro-5-methyl-3(2H)-pyridazinone.

Yield: 15% of theory.

Melting point: 194°–96° C.

C$_{30}$H$_{39}$N$_5$O$_4$×2 HCl (606.6).

| Calculated: | C 59.40 | H 6.81 | N 11.55 | Cl 11.69 |
| Found: | 59.23 | 6.78 | 11.62 | 11.79 |

EXAMPLE 48

6-[2-[2-[3-(4-(2-Isobutoxy-ethyl)phenoxy)-2-hydroxypropylamino]ethyl]benzimidazol-5-yl]-4,5-dihydro-5-methyl-3(2H)-pyridazinone Prepared analogously to Example 1 from 1-[4-(2-isobutoxy-ethyl)-phenoxy]-2,3-epoxypropane and 6-[2-(2-aminoethyl)benzimidazol-5-yl]-4,5-dihydro-5-methyl-3(2H)-pyridazinone.

Yield: 13% of theory, amorphous.

C$_{29}$H$_{39}$N$_5$O$_4$ (521.7).

| Calculated: | C 66.77 | H 7.54 | N 13.43 |
|---|---|---|---|
| Found: | 66.59 | 7.58 | 13.69 |

¹H-NMR spectrum (d₆-DMSO/CD₃OD): δ=0.83 (d,6H); 1.13 (d,3H); 1.7S (m,1H); 2.29 (dd,1H); 2.68–2.80 (m,3H); 3.10–3.20 (m,3H); 3.28(m,2H); 3.99(m,2H); 4.20 (m,1H); 6.89 ) (d,2H); 7.18 (d,2H); 7.45 (d,1H); 7.71(d,1H); 7.90 (s,1H) ppm.

EXAMPLE 49

6-[2-[2-[3-(2-Allyl-phenoxy)-2-hydroxypropylamino]ethyl]benzimidazol-5-yl]-4,5-dihydro-5-methyl-3(2H)-pyridazinone Prepared analogously to Example 1 from 1-(2-allyl-phenoxy)-2,3-epoxypropane and 6-[2-(2-aminoethyl)-benzimidazol-5-yl]-4,5-dihydro-5-methyl-3(2H)-pyridazinone.

Yield: 14% of theory, amorphous.
$C_{26}H_{31}N_5O_3$ (461.6).

| Calculated: | C 67.65 | H 6.77 | N 15.18 |
|---|---|---|---|
| Found: | 67.44 | 6.59 | 15.09 |

¹H-NMR spectrum (d₆-DMSO/CD₃OD): δ=1.13 (d,3H); 2.27 (dd,1H); 2.65–2.90 (m,3H); 3.07 (m,4H); 3.34 (dd,2H); 3.48 (m,1H); 3.90–4.05 (m,3H); 4.93–5.11 (m,2H); 5.85–6.07 (m,1H); 6.80–6.97 (m,2H); 7.05–7.20 (m,2H): 7.48 (d,1H): 7.63 (dd,1H): 7.83 (d,1H) ppm.

EXAMPLE 50

6-[2-[3-(2-Chloro-5-methyl-phenoxy)-2-hydroxypropylamino]ethyl]benzimidazol-5-yl]-4,5-dihydro-5-methyl-3(2H)-pyridazinone Prepared analogously to Example 1 from 1-(2-chloro-5-methyl-phenoxy)-2,3-epoxypropane and 6-[2-(2-aminoethyl)benzimidazol-5-yl]-4,5-dihydro-5-methyl-3(2H)-pyridazinone.

Yield: 33% of theory, amorphous.
$C_{24}H_{28}ClN_5O_3$ (470.0).

| Calculated: | C 61.29 | H 6.00 | N 14.89 | Cl 7.54 |
|---|---|---|---|---|
| Found: | 61.00 | 5.87 | 14.55 | 7.55 |

¹H-NMR spectrum (d₆-DMSO/CD₃OD): δ=1.13 (d,3H); 2.26 (s,3H); 2.26 (dd,1H); 2.65–2.96 (m,3H); 3.00–3.19 (m,4H); 3.48 (m,1H); 4.00 (m,3H); 6.74 (dd,1H); 6.94 (d,1H); 7.23 (d,1H); 7.49 (d,1H); 7.69 (dd,1H); 7.88 (d,1H) ppm.

EXAMPLE 51

6-2-[2-[3-(2-Cyano-phenoxy)-2-hydroxypropylamino]ethyl]benzimidazol-5-yl]-4,5-dihydro-5-methyl-3(2H)-pyridazinone Prepared analogously to Example 1 from 1-(2-cyano-phenoxy)-2,3-epoxypropane and 6-[2-(2-aminoethyl)-benzimidazol-5-yl]-4,5-dihydro-5-methyl-3(2H)-pyridazinone.

Yield: 29% of theory, amorphous. $C_{24}H_{26}N_6O_3$ (446.5).

| Calculated: | C 64.56 | H 5.87 | N 18.82 |
|---|---|---|---|
| Found: | 64.43 | 5.81 | 18.59 |

¹H-NMR spectrum (d₆-DMSO/CD₃OD): δ=1.12 (d,3H); 2.24 (dd,1H); 2.60–2.85 (m,3H); 2.90–3.10 (m,4H); 3.35–3.55 (m,1H); 3.92 (m,1H); 4.02–4.18 (m,2H); 7.08 (t,1H); 7.21 (d,1H); 7.47 (d,1H); 7.55–7.74 (m,3H); 7.83 (d,1H) ppm.

EXAMPLE 52

6-[2-[3-(3-(Naphthyl-1-oxy)-2-hydroxypropylamino)-propyl]benzimidazol-5-yl]-4,5-dihydro-5-methyl-3(2H)-pyridazinone Prepared analogously to Example 1 from 1-(naphthyl-1-oxy)-2,3-epoxypropane and 6-[2-(3-aminopropyl)-benzimidazol-5-yl]-4,5-dihydro-5-methyl-3(2H)-pyridazinone.

Yield: 32% of theory, amorphous.
$C_{28}H_{31}N_5O_3$ (485.6).

| Calculated: | C 69.26 | H 6.44 | N 14.42 |
|---|---|---|---|
| Found: | 69.10 | 6.21 | 14.07 |

¹H-NMR spectrum (d₆-DMSO/CD₃OD): δ=1.11 (d,3H); 2.05 (m,2H); 2.22 (dd,1H); 2.70 (dd,1H); 2.80–3.10 (m,6H); 3.35–3.55 (m,1H); 4.05–4.26 (m,3H); 6.95 (dd,1H); 7.35–7.55 (m,5H); 7.65 (dd,1H); 7.85 (m,2H); 8.23 (dd,1H) ppm.

EXAMPLE 53

6-[2-[2-(3-(2-Cyano-phenoxy)-2-hydroxypropylamino)ethyl]benzimidazol-5-yl]-3(2H)-pyridazinone Prepared analogously to Example 1 from 1-(2-cyano-phenoxy)-2,3-epoxypropane and 6-[2-(2-aminoethyl)-benzimidazol-5-yl]-3(2H)-pyridazinone.

Yield: 19% of theory.
Melting point: 188°–189° C.
$C_{23}H_{22}N_6O_3$ (430.5).

| Calculated: | C 64.17 | H 5.15 | N 19.52 |
|---|---|---|---|
| Found: | 63.92 | 5.14 | 19.62 |

EXAMPLE 54

6-[2-[2-(3-(Naphthyl-1-oxy)-2-hydroxypropylamino)ethyl]benzimidazol-5-yl]-3(2H)-pyridazinone Prepared analogously to Example 1 from 1-(naphthyl-1-oxy)-2,3-epoxypropane and 6-[2-(2-aminoethyl)-benzimidazol-5-yl]-3(2H)-pyridazinone.

Yield: 11% of theory,
Melting point: 196°–197° C.
$C_{26}H_{25}N_5O_3$ (455.5).

| Calculated: | C 68.56 | H 5.53 | N 15.37 |
|---|---|---|---|
| Found: | 68.46 | 5.36 | 15.41 |

EXAMPLE 55

6-[1-[2-[3-(4-(2-Isobutoxy-ethyl)-phenoxy)-2-hydroxypropylamino]ethyl]benzimidazol-5-yl]-4,5-dihydro-5-methyl-3(2H)-pyridazinone Prepared analogously to Example 1 from 1-[4-(2-isobutoxy-ethyl)phenoxy]-2,3-epoxypropane and 6-[1-(2-aminoethyl)benzimidazol-5-yl]-4,5-dihydro-5-methyl-3(2H)-pyridazinone.

Yield: 18% of theory.
Melting point: from 75° C. (sintering).

$R_f$ value: 0.63 (silica gel, dichloromethane/methanol-/ammonia =80:20:0.5).
$C_{29}H_{39}N_5O_4$ (521.6).

| Calculated: | C 66.77 | H 7.54 | N 13.43 |
|---|---|---|---|
| Found: | 66.51 | 7.33 | 13.10 |

EXAMPLE 56

6-[1-[2-[3-(4-(2-Isobutoxy-ethyl)-phenoxy)-2-hydroxypropylamino]-ethyl]benzimidazol-5-yl]-4,5-dihydro-3(2H)-pyridazinone Prepared analogously to Example 1 from 1-[4-(2-isobutoxy-ethyl)-phenoxy]-2,3-epoxypropane and 6-[1-(2-aminoethyl)benzimidazol-5-yl]-4,5-dihydro-3(2H)pyridazinone.
Yield: 22% of theory.
Melting point: 120°–122° C.
$C_{28}H_{37}N_5O_4$ (507.6).

| Calculated: | C 66.25 | H 7.35 | N 13.80 |
|---|---|---|---|
| Found: | 66.08 | 7.32 | 13.94 |

EXAMPLE 57

6-[1-[2-[3-(4-(2-Cyclopropylmethoxy-ethyl)phenoxy)-2-hydroxypropylamino]ethyl]benzimidazol-5-yl]-4,5-dihydro-3(2H)-pyridazinone Prepared analogously to Example 1 from 1-[4-(2-cyclopropylmethoxy-ethyl)phenoxy]-2,3-epoxypropane and 6-[1-(2-aminoethyl)-benzimidazol-5-yl]-4,5-dihydro-3(2H)-pyridazinone.
Yield: 28% of theory.
Melting point: 150°–151° C.
$C_{28}H_{35}N_5O_4$ (505.6).

| Calculated: | C 66.51 | H 6.98 | N 13.85 |
|---|---|---|---|
| Found: | 66.30 | 7.04 | 13.84 |

EXAMPLE 58

6-[1-[2-[3-(4-n-Butylsulphonyloxy-phenoxy)-2-hydroxypropylamino]ethyl]benzimidazol-5-yl]-4,5-dihydro-3(2H)-pyridazinone Prepared analogously to Example 1 from 1-(4-n-butylsulphonyloxy-phenoxy)-2,3-epoxypropane and 6-[1-(2-aminoethyl)benzimidazol-5-yl]-4,5-dihydro-3(2H)-pyridazinone.
Yield: 7% of theory, amorphous.
$R_f$ value: 0.24 (silica gel, dichloromethane/ethanol =80:20).
$C_{26}H_{33}N_6O_6S$ (543.7).

| Calculated: | C 57.44 | H 6.12 | N 12.88 | S 5.90 |
|---|---|---|---|---|
| Found: | 57.39 | 6.23 | 13.03 | 5.74 |

EXAMPLE 59

6-[1-[2-[3-(4-Methylsulphonyloxy-phenoxy)-2-hydroxypropylamino]ethyl]benzimidazol-5-yl]-4,5-dihydro-3(2H)-pyridazinone Prepared analogously to Example 1 from 1-(4-methylsulphonyloxy-phenoxy)-2,3-epoxypropane and 6-[1(2-aminoethyl)benzimidazol-5-yl]-4,5-dihydro-3(2H)-pyridazinone.
Yield: 23% of theory, amorphous.
$C_{23}H_{27}N_5O_6S$ (501.5).

| Calculated: | C 55.08 | H 5.43 | N 13.96 | S 6.39 |
|---|---|---|---|---|
| Found: | 54.90 | 5.46 | 14.20 | 6.54 |

$^1$H-NMR spectrum (CDCl$_3$/CD$_3$OD): δ=2.58–2.90 (m,4H), 3.03–3.20 (m,3H); 3.15 (s,3H); 3.45–3.65 (m,1H); 3.85–4.10 (m,3H); 4.38 (t,2H); 6.88 (dt,2H); 7.19 (dt,2H); 7.50 (d,1H); 7.85 (dd,1H); 8.04 (d,1H); 8.10 (s,1H) ppm.

EXAMPLE 60

6-[1-[2-[3-(4-(2-Cyclobutylmethoxy-ethyl)phenoxy)-2-hydroxypropylamino]ethyl]benzimidazol-5-yl]-4,5-dihydro-3(2H)-pyridazinone Prepared analogously to Example 1 from 1-[4-(2-cyclobutylmethoxyethyl)-phenoxy]-2,3-epoxypropane and 6-[1-(2-aminoethyl)benzimidazol-5-yl]-4,5-dihydro-3(2H)-pyridazinone.
Yield: 13% of theory.
Melting point: from 125° C. (sintering).
$C_{29}H_{37}N_5O_4$ (519.6).

| Calculated: | C 67.03 | H 7.18 | N 13.48 |
|---|---|---|---|
| Found: | 66.81 | 6.94 | 13.47 |

EXAMPLE 61

6-[1-[2-[3-(4-(2-Isopropoxyethoxy-methyl)phenoxy)-2-hydroxypropylamino]ethyl]benzimidazol-5-yl]-4,5-dihydro-3(2H)-pyridazinone-dihydrochloride Prepared analogously to Example 1 from 1-[4-(2-isopropoxyethoxymethyl)phenoxy]-2,3-epoxypropane and 6-[1-(2-aminoethyl)benzimidazol-5-yl]-4,5-dihydro-3(2H)-pyridazinone.
Yield: 13% of theory.
Melting point: from 200° C. (sintering).
$C_{28}H_{37}N_5O_5 \times 2$ HCl (596.5).

| Calculated: | C 56.38 | H 6.59 | N 11.74 | Cl 11.89 |
|---|---|---|---|---|
| Found: | 56.19 | 6.56 | 12.00 | 11.72 |

EXAMPLE 62

6-[1-[3-[3-(4-(2-Isobutoxyethyl)phenoxy)-2hydroxypropylamino]propyl]benzimidazol-5-yl]-4,5-dihydro-3-(2H)-pyridazinone Prepared analogously to Example 1 from 1-[4-(2-isobutoxyethyl)-phenoxy]-2,3-epoxypropane and 6-[1-(3-aminopropyl)benzimidazol-5-yl]-4,5-dihydro-3(2H)-pyridazinone.
Yield: 32% of theory.
Melting point: 132°–134° C.
$C_{29}H_{39}N_5O_4$ (521.67).

| Calculated: | C 66.77 | H 7.54 | N 13.43 |
|---|---|---|---|
| Found: | 66.69 | 7.51 | 13.41 |

EXAMPLE 63

6-[1-[2-[3-(4-(2-Isobutoxyethyl)phenoxy)-2-hydroxypropylamino]-2,2-dimethyl-ethyl]benzimidazol-5-yl]-4,5-dihydro-3(2H)-pyridazinone Prepared analogously to Example 1 from 1-[4-(2-isobutoxyethyl)-phenoxy]-2,3-epoxypropane and 6-[1-(2-amino-2,2-dimethylethyl)benzimidazol-5-yl]-4,5-dihydro-3(2H)-pyridazinone.
Yield: 11% of theory.
Melting point: 130°–132° C.

| Calculated: | C 67.26 | H 7.71 | N 13.07 |
|---|---|---|---|
| Found: | 66.96 | 7.56 | 13.41 |

EXAMPLE 64

6-[1-[2-[3-(4-(2-Isopropoxyethoxy-methyl)phenoxy)-2-hydroxypropylamino]-2,2-dimethyl-ethyl]benzimidazol-5-yl]-4,5-dihydro-3(2H)-pyridazinone Prepared analogously to Example 1 from 1-[4-(2-isopropoxyethoxymethyl)phenoxy]-2,3-epoxypropane and 6-[1-(2-amino-2,2-dimethyl-ethyl)benzimidazol-5-yl]-4,5-dihydro-3(2H)-pyridazinone.
Yield: 9% of theory, amorphous.
$R_f$ value: 0.55 (silica gel, dichloromethane/methanol/ammonia =80:20:0.5).
$C_{30}H_{41}N_5O_5$ (551.7).

| Calculated: | C 65.31 | H 7.49 | N 12.70 |
|---|---|---|---|
| Found: | 65.11 | 7.29 | 12.57 |

EXAMPLE 65

6-[1-[2-[3-(4-(2-Isobutoxyethyl)phenoxy)-2-hydroxypropylamino]ethyl]-2-methyl-benzimidazol-5-yl]-4,5-dihydro-3(2H)-pyridazinone Prepared analogously to Example 1 from 1-[4-(2-isobutoxyethyl)-phenoxy]-2,3-epoxypropane and 6-[1-(2-aminoethyl)-2-methyl-benzimidazol-5-yl]-4,5-dihydro-3(2H)-pyridazinone.
Yield: 28% of theory.
Melting point: 198°–200° C.
$C_{29}H_{39}N_5O_4$ (521.7).

| Calculated: | C 66.77 | H 7.54 | N 13.43 |
|---|---|---|---|
| Found: | 66.56 | 7.53 | 13.30 |

EXAMPLE 66

6-[1-[2-[3-(4-Isopropylsulphonyloxy-phenoxy)-2-hydroxypropylamino]ethyl]-2-methyl-benzimidazol-5-yl]-4,5-dihydro-3(2H)-pyridazinone Prepared analogously to Example 1 from 1-(4-isopropylsulphonyloxy-phenoxy)-2,3-epoxypropane and 6-[1-(2-aminoethyl)-2-methyl-benzimidazol-5-yl]-4,5-dihydro-3(2H)-pyridazinone.
Yield: 31% of theory.
Melting point: 176°–178° C.
$C_{26}H_{33}N_5O_6S$ (543.7).

| Calculated: | C 57.44 | H 6.12 | N 12.88 |
|---|---|---|---|
| Found: | 57.34 | 6.07 | 12.70 |

EXAMPLE 67

6-[1-[2-[3-(4-(2-Cyclopropylmethoxy-ethyl)phenoxy)-2-hydroxypropylamino]ethyl]-2-methyl-benzimidazol-5-yl]-4,5-dihydro-3(2H)-pyridazinone Prepared analogously to Example 1 from 1-[4-(2-cyclopropylmethoxyethyl)phenoxy]-2,3-epoxypropane and 6-[1-(2-aminoethyl)-2-methyl-benzimidazol-5-yl]-4,5-dihydro-3(2H)pyridazinone.
Yield: 21% of theory.
Melting point: 188°–190° C.
$C_{29}H_{37}N_5O_4$ (519.7).

| Calculated: | C 62.68 | H 7.44 | N 12.60 |
|---|---|---|---|
| Found: | 62.59 | 7.31 | 12.42 |

EXAMPLE 68

6-[1-[3-[3-(4-(2-Isobutoxy-ethyl)phenoxy)-2-hydroxypropylamino]propyl]-2-methyl-benzimidazol-5-yl]-4,5-dihydro-3(2H)-pyridazinone Prepared analogously to Example 1 from 1-[4-(2-isobutoxy-ethyl)phenoxy]-2,3-epoxypropane and 6-[1-(3-aminopropyl) -2-methyl-benzimidazol-5-yl]-4,5-dihydro-3(2H)-pyridazinone.
Yield: 6% of theory, amorphous.
$R_f$ value: 0.56 (silica gel, dichloromethane/methanol/ammonia =80:20:0.5).
$C_{30}H_{41}N_5O_4$ (535.7).

| Calculated: | C 67.26 | H 7.72 | N 13.08 |
|---|---|---|---|
| Found: | 67.11 | 7.53 | 13.00 |

EXAMPLE 69

6-[1-[2-[3-(4-(2-Isobutoxy-ethyl)phenoxy)-2-hydroxypropylamino]ethyl]-2-hydroxy-benzimidazol-5-yl]-4,5-dihydro-3(2H)-pyridazinone Prepared analogously to Example 1 from 1-[4-(2-isobutoxy-ethyl)phenoxy]-2,3-epoxypropane and 6-[1-(2-aminoethyl)-2-hydroxy-benzimidazol-5-yl]-4,5-dihydro-3(2H)-pyridazinone.
Yield: 17% of theory.
Melting point: from 110° C. (sintering).
$C_{28}H_{37}N_5O_5$ (523.6).

| Calculated: | C 64.22 | H 7.12 | N 13.38 |
|---|---|---|---|
| Found: | 63.91 | 6.99 | 13.44 |

EXAMPLE 70

6-[1-[2-[3-(4-(2-Cyclopropylmethoxy-ethyl)phenoxy)-2-hydroxypropylamino]ethyl]-2-hydroxy-benzimidazol-5-yl]-4,5-dihydro-3(2H)-pyridazinone Prepared analogously to Example 1 from 1-[4-(2-cyclopropylmethoxyethyl)phenoxy]-2,3-epoxypropane and 6-[1-(2-aminoethyl)-2-hydroxy-benzimidazol-5-yl]-4,5-dihydro-3(2H)-pyridazinone.
Yield: 13% of theory, amorphous.

$R_f$ value: 0.56 (silica gel, dichloromethane/methanol/ammonia =80:20:0.5).
$C_{28}H_{35}N_5O_5$ (521.6).

| Calculated: | C 64.47 | H 6.76 | N 13.43 |
|---|---|---|---|
| Found: | 64.31 | 6.39 | 13.55 |

EXAMPLE 71

6-[1-[2-[3-(4-Isopropylsulphonyloxy-phenoxy)-2-hydroxypropylamino]ethyl]-2-hydroxy-benzimidazol-5-yl]-4,5-dihydro-3(2H)-pyridazinone Prepared analogously to Example 1 from 1-(4-isopropylsulphonyloxy-phenoxy)-2,3-epoxypropane and 6-[1-(2-aminoethyl)-2-hydroxy-benzimidazol-5-yl]-4,5-dihydro-3(2H)-pyridazinone.
Yield: 18% of theory, amorphous
$C_{25}H_{31}N_5O_7S$ (545.6).

| Calculated: | C 55.03 | H 5.73 | N 12.84 | S 5.88 |
|---|---|---|---|---|
| Found: | 54.83 | 5.44 | 12.29 | 5.89 |

$^1$H-NMR spectrum (d$_6$-DMSO/CD$_3$OD): $\delta$=1.42 (d,6H); 2.42 (t,2H); 2.55–2.97 (m,6H); 3.66 (m,1H); 3.74–3.96 (m,5H); 6.93 (d,2H); 7.13–7.25 (m,3H); 7.27–7.43 (m,2H) ppm.

EXAMPLE 72

6-[1-[2-[3-(4-(2-Isobutoxyethyl)phenoxy)-2-hydroxypropyl-amino]ethyl]benztriazol-5-yl]-4,5-dihydro-3(2H)-pyridazinone Prepared analogously to Example 1 from 1-[4-(2-isobutoxyethyl)phenoxy]-2,3-epoxypropane and 6-[1-(2-aminoethyl)benztriazol-5-yl]-4,5-dihydro-3(2H)-pyridazinone.
Yield: 19% of theory, amorphous.
$C_{27}H_{36}N_6O_4$ (508.6).

| Calculated: | C 63.76 | H 7.13 | N 16.53 |
|---|---|---|---|
| Found: | 63.59 | 7.13 | 16.44 |

$^1$H-NMR spectrum (d$_6$-DMSO/CD$_3$OD): $\delta$=0.83 (d,6H); 1.77 (m,1H), 2.55–2.80 (m,4H); 3.03– 3.18 (m,7H); 3.50 (t,2H); 3.75 (m,4H); 4.78 (m,2H); 6.73 (d,2H); 7.10 (d,2H); 7.90 (d,1H); 8.06 (dd,1H); 8.31 (d,1H) ppm.

EXAMPLE 73

6-[1-[2-[3-(4-(2-Cyclobutylmethoxy-ethyl)phenoxy)-2-hydroxypropylamino]ethyl]benztriazol-5-yl]-4,5-dihydro-3(2H)-pyridazinone Prepared analogously to Example 1 from 1-[4-(2-cyclobutylmethoxyethyl)phenoxy]-2,3-epoxypropane and 6- [1-(2-aminoethyl)benztriazol-5-yl]-4,5-dihydro-3(2H)-pyridazinone.
Yield: 17% of theory.
Melting point: 157°–158° C.
$C_{28}H_{36}N_6O_4$ (520.6).

| Calculated: | C 64.60 | H 6.97 | N 16.14 |
|---|---|---|---|
| Found: | 64.50 | 7.04 | 16.22 |

EXAMPLE 74

6-[1-[2-[3-(4-Methylsulphonyloxy-phenoxy)-2-hydroxypropylamino]ethyl]benztriazol-5-yl]-4,5-dihydro-3(2H)-pyridazinone Prepared analogously to Example 1 from 1-(4-methylsulphonyloxy-phenoxy)-2,3-epoxypropane and 6-[1-(2-aminoethyl)benztriazol-5-yl]-4,5-dihydro-3(2H)pyridazinone.
Yield: 23% of theory.
Melting point: 156°–158° C.
$C_{22}H_{26}N_6O_6S$ (502.6).

| Calculated: | C 52.58 | H 5.21 | N 16.72 | S 6.38 |
|---|---|---|---|---|
| Found: | 52.30 | 5.22 | 16.85 | 6.45 |

EXAMPLE 75

6-[1-[2-[3-(4-n-Butylsulphonyloxy-phenoxy)-2-hydroxypropylamino]ethyl]benztriazol-5-yl]-4,5-dihydro-3(2H)-pyridazinone Prepared analogously to Example 1 from 1-(4-n-butylsulphonyloxyphenoxy)-2,3-epoxypropane and 6-[1-(2-aminoethyl)benztriazol-5-yl]-4,5-dihydro-3(2H)-pyridazinone.
Yield: 8% of theory, amorphous.
$R_f$ value: 0.49 (silica gel, dichloromethane/ethanol =9:1).
$C_{25}H_{32}N_6O_6S$ (544.6).

| Calculated: | C 55.13 | H 5.92 | N 15.43 | S 5.89 |
|---|---|---|---|---|
| Found: | 54.99 | 5.51 | 15.30 | 6.02 |

EXAMPLE 76

6-[1-[2-[3-(4-(2-Isobutoxy-ethyl)phenoxy)-2-hydroxypropylamino]ethyl]benzimidazol-5-yl]-3(2H)-pyridazinone Prepared analogously to Example 1 from 1-[4-(2-isobutoxy-ethyl)phenoxy]-2,3-epoxypropane and 6-[1-(2-aminoethyl)benzimidazol-5-yl]-3(2H)-pyridazinone.
Yield: 8% of theory, amorphous.
$C_{28}H_{35}N_5O_4$ (505.6).

| Calculated: | C 64.23 | H 7.12 | N 13.37 |
|---|---|---|---|
| Found: | 64.07 | 7.29 | 13.14 |

$^1$H-NMR spectrum (d$_6$-DMSO/CD$_3$OD): $\delta$=0.80 (d,6H); 1.76 (m,1H); 2.53–2.70 (m,4H); 2.92–3.18 (m,4H); 3.39–3.55 (t,2H); 3.66–3.87 (m,3H); 4.25–4.43 (m,2H); 6.63–7.18 (m,5H); 7.67–7.83 (m,2H); 8.04–8.19 (m,2H); 8.28 (s,1H) ppm.

EXAMPLE 77

6-[1-[2-[3-(4-(2-Cyclopropylmethoxy-ethyl)phenoxy)-2-hydroxypropylamino]ethyl]benzimidazol-5-yl]-3(2H)-pyridazinone Prepared analogously to Example 1 from 1-[4-(2cyclopropylmethoxyethyl)phenoxy]-2,3-epoxypropane and 6-[1-(2-aminoethyl)benzimidazol-5-yl]-3(2H)-pyridazinone.
Yield: 18% of theory.
Melting point: 115°–117° C.
$C_{26}H_{33}N_5O_4$ (503.6)

| Calculated: | C 66.78 | H 6.61 | N 13.91 |
|---|---|---|---|
| Found: | 66.77 | 6.41 | 13.74 |

EXAMPLE 78

6-[1-[2-[3-(4-(2-Cyclobutylmethoxy-ethyl)phenoxy)-2-hydroxypropylamino]ethyl]benzimidazol-5-yl]-3(2H)-pyridazinone Prepared analogously to Example 1 from 1-[4-(2-cyclobutylmethoxyethyl)phenoxy]-2,3-epoxypropane and 6-[1-(2-aminoethyl)benzimidazol-5-yl]-3(2H)-pyridazinone.
Yield: 13% of theory, amorphous.
$C_{29}H_{35}N_5O_4$ (517.6).

| Calculated: | C 67.29 | H 6.82 | N 13.53 |
|---|---|---|---|
| Found: | 67.00 | 6.71 | 13.52 |

$^1$H-NMR spectrum (d$_6$-DMSO/CD$_3$OD):
δ=1.60–2.04 (m,7H); 2.38–2.55 (m,2H); 2.71 (t,2H); 3.32 (t,2H); 3.51 (t,2H); 3.93–4.05 (m,2H); 4.27–4.46 (m,3H); 4.54 (t,2H); 6.82 (d,2H); 7.00–7.18 (m,3H); 7.73 (d,1H); 7.86 (dd,1H); 8.11 (d,1H); 8.20 (d,1H); 8.30 (s,1H) ppm.

EXAMPLE 79

6-[4-[3-[3-(4-(2-Isobutoxyethyl)phenoxy)-2-hydroxypropylamino]propylsulphonyl]phenyl]-4,5-dihydro-3(2H)-pyridazinone Prepared analogously to Example 1 from 1-[4-(2isobutoxyethyl)phenoxy]-2,3-epoxypropane and 6-[4-(3-aminopropylsulphonyl]phenyl]-3(2H)-pyridazinone.
Yield: 24% of theory.
Melting point: 129°–131° C.
$C_{28}H_{39}N_3O_6S$ (545.7).

| Calculated: | C 61.63 | H 7.20 | N 7.70 | S 5.88 |
|---|---|---|---|---|
| Found: | 61.43 | 6.95 | 7.53 | 6.07 |

EXAMPLE 80

6-[4-[3-[3-(4-(2-Cyclopropylmethoxyethyl)phenoxy)-2-hydroxypropylamino]propylsulphonyl]phenyl]-4,5-dihydro-3(2H)-pyridazinone Prepared analogously to Example 1 from 1-[4-(2-cyclopropylmethoxyethyl)phenoxy]-2,3-epoxypropane and 6-[4-(3-aminopropylsulphonyl]phenyl]-3(2H)-pyridazinone.
Yield: 24% of theory.
Melting point: 128°–130° C.
$C_{28}H_{37}N_3O_6S$ (543.69).

| Calculated: | C 61.86 | H 6.86 | N 7.73 | S 5.90 |
|---|---|---|---|---|
| Found: | 61.75 | 7.09 | 7.60 | 6.06 |

EXAMPLE 81

6-[4-[3-[3-(4-(2-Isopropoxyethoxymethyl)phenoxy)-2-hydroxypropylamino]propylsulphonyl]phenyl]-4,5-dihydro-3(2H)-pyridazinone Prepared analogously to Example 1 from 1-[4-(2-isopropoxyethoxymethyl)phenoxy]-2,3-epoxypropane and 6-[4-(3-aminopropylsulphonyl)phenyl]-3(2H)-pyridazinone.
Yield: 23% of theory.
Melting point: 108°–110° C.
$C_{28}H_{39}N_3O_7S$ (561.7).

| Calculated: | C 59.87 | H 7.00 | N 7.48 | S 5.71 |
|---|---|---|---|---|
| Found: | 59.76 | 6.81 | 7.56 | 5.99 |

EXAMPLE 82

6-[4-[2-[3-(Naphthyl-1-oxy)-2-hydroxypropylamino]ethyl]phenyl]-4,5-dihydro-3(2H)-pyridazinone-hydrochloride Prepared analogously to Example 1 from 1-(naphthyl-1-oxy)-2,3-epoxypropane and 6-[4-(2-aminoethyl)-phenyl]-4,5-dihydro-3(2H)-pyridazinone.
Yield: 33% of theory.
Melting point: 177°–180° C.
$C_{25}H_{27}N_3O_3 \times HCl$ (454.0).

| Calculated: | C 66.14 | H 6.22 | N 9.26 | S 7.81 |
|---|---|---|---|---|
| Found: | 65.99 | 6.21 | 9.35 | 7.76 |

EXAMPLE 83

6-[4-[2-[3-(4-(2-Cyclobutylmethoxyethyl)phenoxy)-2-hydroxypropylamino]ethyl]phenyl]-4,5-dihydro-3(2H)-pyridazinone Prepared analogously to Example 1 from 1-[4-(2cyclobutylmethoxyethyl)phenoxy]-2,3-epoxypropane and 6-[4-(2-aminoethyl)phenyl]-4,5-dihydro-3(2H)-pyridazinone.
Yield: 24% of theory.
Melting point: from 119° C. (sintering).
$C_{28}H_{37}N_3O_4$ (479.6).

| Calculated: | C 70.12 | H 7.78 | N 8.76 |
|---|---|---|---|
| Found: | 69.94 | 7.79 | 8.67 |

EXAMPLE 84

6-[4-[2-[3-(Naphthyl-1-oxy)-2-hydroxypropylamino]ethyl]phenyl]-3(2H)-pyridazinone-hydrochloride Prepared analogously to Example 1 from 1-(naphthyl-1-oxy)-2,3-epoxypropane and 6-[4-(2-aminoethyl)-phenyl]-3(2H)-pyridazinone.
Yield: 16% of theory.
Melting point: 219°–222° C.
$C_{25}H_{25}N_3O_3 \times HCl$ (452.0).

| Calculated: | C 66.43 | H 5.80 | N 9.30 | Cl 7.84 |
|---|---|---|---|---|
| Found: | 66.42 | 5.97 | 9.30 | 8.01 |

EXAMPLE 85

6-[4-[2-[3-(4-(2-Cyclobutylmethoxyethyl)phenoxy)-2-hydroxypropylamino]ethyl]phenyl]-3(2H)-pyridazinone Prepared analogously to Example 1 from 1-[4-(2-cyclobutylmethoxyethyl)phenoxy]-2,3-epoxypropane and 6-[4-(2-aminoethyl)phenyl]-3(2H)-pyridazinone.
Yield: 10% of theory.

Melting point: 119°–121° C.
$C_{28}H_{35}N_3O_4$ (477.6).

| Calculated: | C 70.42 | H 7.39 | N 8.80 |
|---|---|---|---|
| Found: | 70.31 | 7.39 | 8.76 |

EXAMPLE 86

6-[4-[2-[3-(Naphthyl-1-oxy)-2-hydroxypropylamino]-ethylaminocarbonylmethyl]phenyl]-4,5-dihydro-3(2H)-pyridazinone-hydrochloride Prepared analogously to Example 1 from 1-(naphthyl-1-oxy)-2,3-epoxypropane and 6-[4-((2-aminoethyl)aminocarbonylmethyl)phenyl]-3(2H)-pyridazinone.
Yield: 12% of theory, amorphous.
$C_{27}H_{30}N_4O_4 \times HCl$ (511.1).

| Calculated: | C 63.45 | H 6.11 | N 10.96 | Cl 6.94 |
|---|---|---|---|---|
| Found: | 63.60 | 6.25 | 10.75 | 7.03 |

$^1$H-NMR spectrum (d$_6$-DMSO/CD$_3$OD): δ=2.40–2.55 (m,2H); 2.88–3.57 (m,9H); 4.08–4.22 (m,3H); 4.32 (m,1H); 6.98 (dd,1H); 7.29–7.73 (m,8H); 7.83–7.91 (m,1H); 8.22–8.35 (m,1H) ppm.

EXAMPLE 87

6-[4-[2-[3-(4-(2-Cyclobutylmethoxyethyl)phenoxy)-2-hydroxypropylamino]ethylaminocarbonylmethyl]-phenyl]-4,5-dihydro-3(2H)-pyridazinone-hydrochloride Prepared analogously to Example 1 from 1-[4-(2-cyclobutylmethoxyethyl)phenoxy]-2,3-epoxypropane and 6-[4-((2-aminoethyl)aminocarbonylmethyl)phenyl]-4,5-dihydro-3(2H)-pyridazinone.
Yield: 12% of theory.
Melting point: 214°–216° C.
$C_{30}H_{40}N_4O_5 \times HCl$ (573.1).

| Calculated: | C 62.87 | H 7.21 | N 9.78 |
|---|---|---|---|
| Found: | 62.75 | 7.03 | 9.77 |

EXAMPLE 88

6-[3-[2-[3-(4-(2-Cyclobutylmethoxyethyl)phenoxy)-2-hydroxypropylamino]ethoxy]phenyl]-3(2H)-pyridazinone Prepared analogously to Example 1 from 1-[4-(2-cyclobutylmethoxyethyl)phenoxy]-2,3-epoxypropane and 6-[3-(2-aminoethoxy)phenyl]-3(2H)-pyridazinone.
Yield: 11% of theory.
Melting point: 111°–112° C.
$C_{28}H_{35}N_3O_5$ (493.6).

| Calculated: | C 68.13 | H 7.15 | N 8.51 |
|---|---|---|---|
| Found: | 67.95 | 7.10 | 8.50 |

EXAMPLE 89

6-[4-[2-[3-(4-(2-Isopropoxyethoxy-methyl)phenoxy)-2-hydroxypropylamino]ethoxy]-3-methyl-phenyl]-3(2H)-pyridazinone Prepared analogously to Example 1 from 1-[4-(2-isopropoxyethoxymethyl)phenoxy]-2,3-epoxypropane and 6-[4-(2-aminoethoxy)-3-methyl-phenyl]-3(2H)-pyridazinone.
Yield: 35% of theory.
Melting point: 121°–122° C.
$C_{28}H_{37}N_3O_6$ (511.6).

| Calculated: | C 65.73 | H 7.29 | N 8.21 |
|---|---|---|---|
| Found: | 65.51 | 7.14 | 8.10 |

EXAMPLE 90

6-[4-[2-[3-(4-(2-Phenoxyethoxy-methyl)phenoxy)-2-hydroxypropylamino]ethoxy]-3-chloro-phenyl]-4,5-dihydro-3(2H)-pyridazinone Prepared analogously to Example 1 from 1-[4-(2-phenoxyethoxymethyl)phenoxy]-2,3-epoxypropane and 6-[4-(2-aminoethoxy)-3-chloro-phenyl]-4,5-dihydro-3-(2H)-pyridazinone.
Yield: 28% of theory.
Melting point: 95°–97° C.
$C_{30}H_{34}ClN_3O_6$ (568.10).

| Calculated: | C 63.43 | H 6.03 | N 7.40 | Cl 6.24 |
|---|---|---|---|---|
| Found: | 63.35 | 5.97 | 7.44 | 6.44 |

EXAMPLE 91

6-[4-[2-[3-(4-(2-Phenoxyethoxy-methyl)phenoxy)-2-hydroxypropylamino]ethoxy]-3-methyl-phenyl]-4,5-dihydro-3-(2H)-pyridazinone Prepared analogously to Example 1 from 1-[4-(2-phenoxyethoxymethyl)phenoxy]-2,3-epoxypropane and 6-[4-(2-aminoethoxy)-3-methyl-phenyl]-4,5-dihydro-3-(2H)-pyridazinone.
Yield: 26% of theory.
Melting point: 85°–87° C.
$C_{31}H_{37}N_3O_6$ (547.70).

| Calculated: | C 67.98 | H 6.81 | N 7.67 |
|---|---|---|---|
| Found: | 67.89 | 7.01 | 7.81 |

EXAMPLE 92

6-[4-[2-[3-(4-(2-n-Butyloxyethoxy-methyl)phenoxy)-2-hydroxypropylamino]ethoxy]-3-methyl-phenyl]-4,5-dihydro-3-(2H)-pyridazinone Prepared analogously to Example 1 from 1-[4-(2-n-butyloxyethoxymethyl)phenoxy]-2,3-epoxypropane and 6-[4-(2-aminoethoxy)-3-methyl-phenyl]-4,5-dihydro-3-(2H)-pyridazinone.
Yield: 28% of theory.
Melting point: 96°–98° C.
$C_{29}H_{41}N_3O_6$ (527.70).

| Calculated: | C 66.00 | H 7.83 | N 7.96 |
|---|---|---|---|
| Found: | 65.88 | 7.95 | 7.80 |

EXAMPLE 93

6-[4-[2-[3-(4-(2-n-Butyloxyethoxy-methyl)phenoxy)-2-hydroxypropylamino]ethoxy]-3-chloro-phenyl]-4,5-dihydro-3-(2H)-pyridazinone Prepared analogously to Example 1 from 1-[4-(2-n-butyloxyethoxymethyl)phenoxy]-2,3-epoxypropane and 6-[4-(2-aminoethoxy)-3-chloro-phenyl]-4,5-dihydro-3-(2H)-pyridazinone.
Yield: 27% of theory.
Melting point: 108°–110° C.
$C_{28}H_{38}ClN_3O_6$ (548.10).

| Calculated: | C 61.36 | H 6.99 | N 7.67 | Cl 6.47 |
|---|---|---|---|---|
| Found: | 61.51 | 6.85 | 7.61 | 6.54 |

EXAMPLE 94

6-[4-[2-[3-(4-(2-n-Butyloxyethoxy-methyl)phenoxy)-2-hydroxypropylamino]ethoxy]phenyl]-4,5-dihydro-3-(2H)-pyridazinone Prepared analogously to Example 1 from 1-[4-(2-n-butyloxyethoxymethyl)phenoxy]-2,3-epoxypropane and 6-[4-(2-aminoethoxy)phenyl]-4,5-dihydro-3-(2H)-pyridazinone.
Yield: 30% of theory.
Melting point: 82°–84° C.
$C_{28}H_{39}N_3O_6$ (513.60).

| Calculated: | C 65.48 | H 7.65 | N 8.18 |
|---|---|---|---|
| Found: | 65.31 | 7.74 | 8.16 |

EXAMPLE 95

6-[4-[2-[3-(4-(2-Methoxyethoxy-methyl)phenoxy)-2-hydroxypropylamino]ethoxy]-3-methyl-phenyl]-3-(2H)-pyridazinone Prepared analogously to Example 1 from 1-[4-(2-methoxyethoxymethyl)phenoxy]-2,3-epoxypropane and 6-[4-(2-aminoethoxy)-3-methyl-phenyl]-3(2H)-pyridazinone.
Yield: 32% of theory.
Melting point: 127°–128°∞ C.
$C_{26}H_{33}N_3O_6$ (483.55).

| Calculated: | C 64.58 | H 6.88 | N 8.69 |
|---|---|---|---|
| Found: | 64.42 | 6.71 | 8.44 |

In the pharmaceutical Examples which follow, any suitable compound of formula I can be used as the active substance, e.g. the compounds of the preceding Examples.

EXAMPLE 96

| Ampoules containing 100 mg of active substance per 5 ml | |
|---|---|
| Active substance | 100 mg |
| Methyl glucamine | 35 mg |
| Glycofurol | 1000 mg |
| Polyethyleneglycol-polypropyleneglycol block polymer | 250 mg |
| Water for injections ad | 5 ml |

Preparation

Methyl glucamine is dissolved in some of the water and the active substance is dissolved with stirring and heating. After the addition of the solvent the solution is made up to the required volume using water.

EXAMPLE 97

| Tablets containing 50 mg of active substance | |
|---|---|
| Active substance | 50.0 mg |
| Calcium phosphate | 70.0 mg |
| Lactose | 40.0 mg |
| Corn starch | 35.0 mg |
| Polyvinylpyrrolidone | 3.5 mg |
| Magnesium stearate | 1.5 mg |
| | 200.0 mg |

Preparation

The active substance, CaHPO, lactose and corn starch are uniformly moistened with an aqueous PVP solution. The mass is passed through a 2 mm screen, dried at 50° C. in a circulating air dryer and screened again.

After the addition of the lubricant the granules are compressed in a tablet making machine.

EXAMPLE 98

| Coated tablets containing 50 mg of active substance | |
|---|---|
| Active substance | 50.0 mg |
| Lysine | 25.0 mg |
| Lactose | 60.0 mg |
| Corn starch | 34.0 mg |
| Gelatin | 10.0 mg |
| Magnesium stearate | 1.0 mg |
| | 180.0 mg |

Preparation

The active substance is mixed with the excipients and moistened with an aqueous gelatin solution. After screening and drying the granules are mixed with magnesium stearate and compressed to form cores. The cores thus produced are coated by known methods. Dyestuff may be added to the coating suspension or solution.

EXAMPLE 99

| Coated tablets containing 100 mg of active substance | |
|---|---|
| Active substance | 100.0 mg |
| Lysine | 50.0 mg |
| Lactose | 86.0 mg |
| Corn starch | 50.0 mg |
| Polyvinylpyrrolidone | 2.8 mg |
| Microcrystalline cellulose | 60.0 mg |
| Magnesium stearate | 1.2 mg |
| | 350.0 mg |

Preparation

The active substance is mixed with the excipients and moistened with an aqueous PVP solution. The moist mass is passed through a 1.5 mm screen and dried at 45° C. After drying it is screened again and the magnesium stearate is added. This mixture is compressed to form cores.

The cores thus produced are coated by known methods. Dyestuffs may be added to the coating suspension or solution.

EXAMPLE 100

| Capsules containing 250 mg of active substance | |
| --- | --- |
| Active substance | 250.0 mg |
| Corn starch | 68.5 mg |
| Magnesium stearate | 1.5 mg |
| | 320.0 mg |

Preparation

The active substance and corn starch are mixed together and moistened with water. The moist mass is screened and dried. The dry granules are screened and mixed with magnesium stearate. The finished mixture is packed into size 1 hard gelatine capsules.

EXAMPLE 101

| Oral suspension containing 50 mg of active substance per 5 ml | |
| --- | --- |
| Active substance | 50.0 mg |
| Hydroxyethylcellulose | 50.0 mg |
| Sorbic acid | 5.0 mg |
| 70% sorbitol | 600.0 mg |
| Glycerol | 200.0 mg |
| Flavouring | 15.0 mg |
| Water ad | 5.0 ml |

Preparation

Distilled water is heated to 70° C. Hydroxyethylcellulose is dissolved therein with stirring. The solution is cooled to ambient temperature by the addition of sorbitol solution and glycerol.

At ambient temperature the sorbic acid, flavouring and active substance are added. To eliminate air from the suspension it is evacuated with stirring. One dose = 50 mg is contained in 5.0 ml.

EXAMPLE 102

| Suppositories containing 100 mg of active substance | |
| --- | --- |
| Active substance | 100.0 mg |
| Solid fat | 1600.0 mg |
| | 1700.0 mg |

Preparation

The hard fat is melted. At 40° C. the ground active substance is homogeneously dispersed in the melt. It is cooled to 38° C. and poured into slightly chilled suppository moulds.

What is claimed is:

1. A 2-Hydroxy-n-propylamine of the formula $$R_1-O-CH_2-CHOH-CH_2-NH-A-R_2 \quad (I)$$

wherein $R_1$ represents a naphthyl group, a phenyl group substituted by a $C_{1-5}$-alkylsulphonyloxy or by an allyl, allyloxy, cyano or aminocarbonylmethyl group, a phenyl group substituted by a $C_{1-3}$alkyl group, wherein the alkyl moiety is substituted in the 1-, 2- or 3-position by an alkoxy, cycloalkyloxy, cycloalkylmethoxy, 2-alkoxyethoxy, 2-cycloalkyloxyethoxy, 2- cycloalkylmethoxy-ethoxy or 2-phenoxyethoxy group, wherein the alkoxy moiety may have from 1 to 6 carbon atoms and the cycloalkyl or cycloalkyloxy part may have 3 to 6 carbon atoms, or a phenyl group disubstituted by a $C_{1-3}$ alkyl group and by a halogen atom, A represents a straight-chained $C_{2-4}$ alkylene group optionally substituted by one or two $C_{1-3}$ alkyl groups and $R_2$ represents a group of formula wherein $R_3$ represents a hydrogen atom or a $C_{1-3}$ alkyl group, $R_4$ and $R_5$ each represents a hydrogen atom or together they represent another carbon-carbon bond and B represents a group of formula wherein $X_1$ represents a CH group optionally substituted by a hydroxy group or by a $C_{1-3}$ alkyl group, and $Y_2$ represents a bond or an imino group, or a pharmaceutically acceptable acid addition salt thereof.

2. A 2-hydroxy-n-propylamine of formula I according to claim 1, wherein $R_1$ represents a naphthyl, allylphenyl, allyloxyphenyl, cyanophenyl, aminocarbonyl-methylphenyl or chloro-methylphenyl group, an alkysulphonyloxyphenyl group with 1 to 4 carbon atoms in the alkyl moiety or a phenyl group substituted in the 4-position by a 2-alkoxyethyl, 2-cycloalkylmethoxyethyl, 2-alkoxyethoxymethyl, 2-cycloalkyloxy-ethoxymethyl, 2-cycloalkylmethoxyethoxymethyl or 2-phenoxyethoxymethyl group, wherein the alkoxy moiety may have 1 to 4 carbon atoms and the cycloalkyl or cycloalkyloxy part may have 3 or 4 carbon atoms, A represents a $C_{2-4}$ n-alkylene group optionally mono- or disubstituted by a methyl group in the α-position with respect to the adjacent nitrogen atom and $R_2$ represents a group of the formula

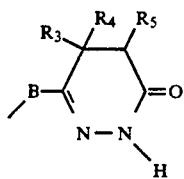

wherein
R3 represents a hydrogen atom or a methyl group,
R4 and R5 each represent a hydrogen atom or together they represent another carbon-carbon bond and
B represents a group of the formula

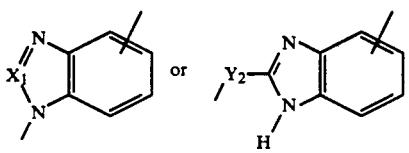

wherein
X1 represents a CH group optionally substituted by a hydroxy or methyl group, and
Y2 represents a bond or an imino group,
or a pharmaceutically acceptable acid addition salt thereof.

3. A 2-hydroxy-n-propylamine of formula I according to claim 1, wherein
R1 represents a naphthyl, allylphenyl, allyloxyphenyl or chloro-methylphenyl group or a phenyl group substituted in the 4-position by a 2-alkoxyethyl, 2-cycloalkylmethoxyethyl, 2-alkoxyethoxymethyl, 2-cycloalkyloxyethoxymethyl, 2-cycloalkylmethoxyethoxymethyl or 2-phenoxyethoxymethyl group, wherein the alkoxy moiety may have 1 to 3 carbon atoms and the cycloalkyl or cycloalkyloxy moiety may have 3 or 4 carbon atoms,
A represents a C2-4 n-alkylene group optionally disubstituted by methyl groups in the α-position with respect to the adjacent nitrogen atom and
R2 represents a group of the formula

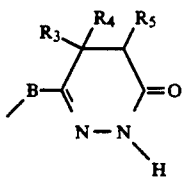

wherein
R3 represents a hydrogen atom or a methyl group,
R4 and R5 each represent a hydrogen atom or together they represent another carbon-carbon bond and
B represents a group of formula

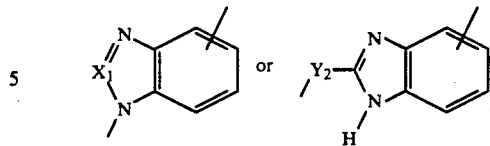

wherein
X1 represents a CH group, and
Y2 represents a bond or an imino group,
or a pharmaceutically acceptable acid addition salt thereof.

4. A 2-hydroxy-n-propylamine of formula I according to claim 1, selected from the group consisting of:
6-[1-[2-[3-(4-(2-cyclobutylmethoxy-ethyl)phenoxy)-2-hydroxy-propylamino]ethyl]benzimidazol-5yl]-4,5-dihydro-3(2H)-pyridazinone,
6-[1-[2-[3-(4-(2-cyclopropylmethoxy-ethyl)phenoxy)-2-hydroxypropylamino]ethyl]benzimidazol-5-yl]-4,5-dihydro-3(2H)-pyridazinone,
6-[1-[3-[3-(4-(2-isobutoxyethyl)phenoxy)-2-hydroxy-propylamino]propyl]benzimidazol-5-yl]4,5-dihydro-3(2H)-pyridazinone,
6-[1-[2-[3-(4-(2-isobutoxyethyl)phenoxy)-2-hydroxy-propylamino]-2,2-dimethylethyl]benzimidazol-5-yl]-4,5-dihydro-3(2H)-pyridazinone,
and pharmaceutically acceptable salts thereof.

5. A compound of the formula I, in accordance with claim 3, wherein R1 represents a phenyl group substituted in the 4-position by a 2-alkoxyethyl, 2-cycloalkoxymethoxyethyl, 2-alkoxyethoxymethyl, 2-cycloalkyloxyethoxymethyl, 2-cycloalkylmethoxyethoxymethyl or 2-phenoxyethoxymethyl group, wherein the alkoxy moiety may have 1 to 3 carbon atoms and the cycloalkyl or cycloalkyloxy moiety may have 3 to 4 carbon atoms and
b represents a group of the formula

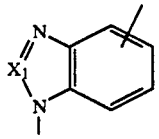

or a pharmaceutically acceptable acid addition salt thereof.

6. A pharmaceutical composition suitable for the treatment of myocardial ischaemia (angina), cardiac insufficiency after myocardial infarct, or hypertension, comprising a therapeutic amount of a compound of formula I, according to claims 1, 2, 3, 4 or 5 and a pharmaceutically acceptable carrier.

7. A method for treating myocardial ischaemia which comprises administering to a warm blooded animal suffering from one of said conditions a therapeutic amount of a compound of formula I, as set forth in claims 1, 2, 3, 4, 5 or 6.

8. A method for treating cardiac insufficiency after myocardial infarct which comprises administering to a warm blooded animal suffering from one of said conditions a therapeutic amount of a compound of formula I, as set forth in claims 1, 2, 3, 4, 5, or 6.

9. A method for treating hypertension which comprises administering to a warm blooded animal suffering from one of said conditions a therapeutic amount of a compound of formula I, as set forth in claims 1, 2, 3, 4, 5 or 6.

* * * * *